(12) United States Patent
Takebe et al.

(10) Patent No.: US 7,498,393 B2
(45) Date of Patent: Mar. 3, 2009

(54) FLUORINATED COMPOUND, FLUOROPOLYMER, RESIST COMPOSITION, AND COMPOSITION FOR RESIST PROTECTIVE FILM

(75) Inventors: Yoko Takebe, Yokohama (JP); Masataka Eda, Yokohama (JP); Osamu Yokokoji, Yokohama (JP); Takashi Sasaki, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 11/626,913

(22) Filed: Jan. 25, 2007

(65) Prior Publication Data
US 2007/0154844 A1 Jul. 5, 2007

Related U.S. Application Data

(63) Continuation of application No. PCT/JP2005/013507, filed on Jul. 22, 2005.

(30) Foreign Application Priority Data

| Jul. 30, 2004 | (JP) | 2004-223363 |
| Nov. 25, 2004 | (JP) | 2004-340595 |
| May 24, 2005 | (JP) | 2005-151028 |

(51) Int. Cl.
*C08F 136/16* (2006.01)

(52) U.S. Cl. ............... 526/252; 430/270.1; 430/914; 430/945; 526/242

(58) Field of Classification Search ......... 430/270.1, 430/914, 945; 526/252, 242
See application file for complete search history.

(56) References Cited

U.S. PATENT DOCUMENTS

| 5,510,406 | A | 4/1996 | Matsuo et al. |
| 6,310,142 | B1 * | 10/2001 | Apostolo et al. ......... 525/200 |
| 6,670,511 | B2 * | 12/2003 | Kashiwagi et al. ....... 568/683 |
| 6,733,952 | B2 | 5/2004 | Kaneko et al. |
| 6,815,146 | B2 | 11/2004 | Okada et al. |
| 6,818,258 | B2 | 11/2004 | Kaneko et al. |
| 6,858,692 | B2 * | 2/2005 | Kaneko et al. ........... 526/252 |
| 6,916,590 | B2 | 7/2005 | Kaneko et al. |
| 6,984,704 | B2 * | 1/2006 | Kodama et al. .......... 526/250 |
| 7,015,366 | B2 * | 3/2006 | Kodama et al. .......... 568/840 |
| 7,026,416 | B2 | 4/2006 | Kawaguchi et al. |
| 7,091,294 | B2 | 8/2006 | Takebe et al. |
| 2005/0202345 | A1 | 9/2005 | Kawaguchi et al. |
| 2005/0234206 | A1 * | 10/2005 | Takebe et al. ............. 526/245 |
| 2006/0004164 | A1 * | 1/2006 | Kodama et al. ........... 526/249 |
| 2006/0122348 | A1 * | 6/2006 | Takebe et al. ............. 526/252 |
| 2006/0135663 | A1 * | 6/2006 | Takebe et al. ............. 524/157 |
| 2006/0188816 | A1 | 8/2006 | Takebe et al. |
| 2007/0207409 | A1 * | 9/2007 | Takebe et al. ............ 430/270.1 |

FOREIGN PATENT DOCUMENTS

| EP | 1 365 290 A1 | 11/2003 |
| EP | 1 367 071 A | 12/2003 |
| EP | 1772468 * | 4/2007 |
| JP | 4-189880 | 7/1992 |
| JP | 4-204848 | 7/1992 |
| JP | 6-220232 | 8/1994 |
| WO | WO 02/064648 A1 | 8/2002 |
| WO | WO-02/064648 A1 * | 8/2002 |
| WO | WO 2004/074937 A1 | 9/2004 |

OTHER PUBLICATIONS

M. Eda, et al., "Novel Fluoropolymers for Next Generation Lithographic Material -Relationship between Structure and Performances-", Reports Res. Lab. Asahi Glass Co., Ltd., 54, pp. 41-48, 2004.
U.S. Appl. No. 11/593,549, filed Nov. 7, 2006, Eda, et al.
U.S. Appl. No. 07/698,078, filed May 10, 1991, Matsuo, et al.
U.S. Appl. No. 11/746,316, filed May 9, 2007, Takebe, et al.
U.S. Appl. No. 11/626,913, filed Jan. 25, 2007, Takebe, et al.

* cited by examiner

*Primary Examiner*—Peter D. Mulcahy
*Assistant Examiner*—Henry Hu
(74) *Attorney, Agent, or Firm*—Oblon, Spivak, McClelland, Maier & Neustadt, P.C.

(57) ABSTRACT

A fluoropolymer having functional groups and having high transparency in a wide wavelength range is provided, and a resist composition and a composition for a resist protective film, comprising the fluoropolymer, wherein the fluoropolymer has monomer units formed by cyclopolymerization of a fluorinated diene represented by the formula (1):

$$CF_2=CFCF_2C(CF_3)(OR^1)-(CH_2)_nCR^2=CHR^3 \qquad (1)$$

wherein $R^1$ is a hydrogen atom, an alkyl group having at most 20 carbon atoms, or $(CH_2)_aCOOR^4$ (wherein a is 0 or 1, and $R^4$ is a hydrogen atom or an alkyl group having at most 20 carbon atoms), each of $R^2$ and $R^3$, which are independent of each other, is a hydrogen atom or an alkyl group having at most 12 carbon atoms, and n is 0 or 2, provided that when n is 0, at least one of $R^1$, $R^2$ and $R^3$ is other than a hydrogen atom.

10 Claims, No Drawings

FLUORINATED COMPOUND, FLUOROPOLYMER, RESIST COMPOSITION, AND COMPOSITION FOR RESIST PROTECTIVE FILM

TECHNICAL FIELD

The present invention relates to a novel fluorinated compound, a fluoropolymer and a process for its production, and a resist composition or a composition for a resist protective film, containing the fluoropolymer.

BACKGROUND ART

As fluoropolymers having functional groups, functional group-containing fluoropolymers are known which are used for fluorinated ion exchange membranes, curable fluorinated resin coating materials, etc. However, they are all basically straight chained polymers, and they are obtainable by copolymerization of a fluoroolefin represented by tetrafluoroethylene with a monomer having a functional group.

Further, a polymer containing functional groups and having a fluorinated alicyclic structure in its main chain, is also known. As a method for introducing functional groups to the polymer having a fluorinated alicyclic structure in its main chain, a method of utilizing terminal groups of a polymer obtained by polymerization, a method of subjecting a polymer to high temperature treatment to oxidize and decompose side chains or terminals of the polymer to form functional groups, or a method of copolymerizing a monomer having a functional group, and if necessary, adding treatment such as hydrolysis, to introduce functional groups, is, for example, known (see Patent Documents 1, to 4).

The above-mentioned methods are available as methods for introducing functional groups to a polymer having a fluorinated alicyclic structure in its main chain. However, the method for introducing functional groups by treating the terminal groups of the polymer, has a drawback that the functional group concentration is low, and no adequate characteristics of the functional groups can be obtained. Whereas, by the method for introducing functional groups by copolymerizing a monomer having a functional group, there will be a problem such that if the functional group concentration is increased, the mechanical properties tend to deteriorate due to a decrease of the glass transition temperature (Tg).

A resist material utilizing an acid catalytic reaction in a reaction mechanism, such as a chemical amplification resist, is patterned through a process of e.g. formation of a resist coating film, exposure, baking after the exposure and development. It is known that, during the patterning, an acid produced by irradiation of active chemical rays is deactivated by a reaction with a compound reactive with an acid, such as an amine floating in the air as an impurity, whereby formation of a resist image is hindered or a change in sensitivity occurs. Such a problem is described in e.g. Non-Patent Document 1. To be left between the exposure and the baking after exposure, presents a substantial adverse effect to the properties of the resist. Namely, a PED effect (Post Exposure Delay effect) is well known, wherein the resist sensitivity abruptly decreases and thus no pattern formation tends to be formed in a case of prolongation of the time to be left between the exposure and the baking after exposure.

As one of methods to lower the PED effect, a method is known wherein a polymer film (resist protective film) not compatible with a resist film is formed on the resist film, as disclosed in e.g. Patent Document 5. This method is a method for forming the resist protective film to prevent an amine or the like floating in the air from entering into the resist film. Such a method has a drawback that the number of process steps increases by the steps for formation and removal of the resist protective film.

Further, in order not to impair the properties of the resist material, it is necessary that the resist protective film be "transparent" to radiation such as X-rays or ultraviolet rays to be used in the resist process. Namely, the composition for a resist protective film is also required not to absorb radiation such as X-rays or ultraviolet rays and not to undergo a side reaction such as insolubilization. However, most of materials to be used for the composition for a resist protective film which are considered to have an effect of suppressing the PED effect, fail to satisfy the above conditions.

Particularly for ArF excimer laser (193 nm) or $F_2$ excimer laser (157 nm), no compositions for a resist protective film have heretofore been found, which have both transparency and an effect of sufficiently suppressing the PED effect.

On the other hand, by the liquid immersion exposure technique, exposure at high resolution will be possible by employing a liquid having a high refractive index between a lens and a resist film, but there are problems such that the resist film swells, and impurities produced from the resist film are dissolved in an upper portion of the liquid thereby causing contamination of the lens.

As one of the methods to solve such problems, it is desired to employ a method wherein a resist film is coated with a composition for a resist protective film not compatible with both the liquid having a high refractive index and the resist film, and further capable of lowering the PED effect as mentioned above.

For example, Patent Document 6 discloses that a cyclic or linear perfluoroalkyl polyether is effective as a material for forming a resist protective film. However, there are no disclosure about lowering of the PED effect, and a perfluoroorganic compound is used to remove the resist protective film, which makes the process cumbersome.

Patent Document 1: JP-A-4-189880
Patent Document 2: JP-A-4-226177
Patent Document 3: JP-A-6-220232
Patent Document 4: WO02/064648
Patent Document 5: JP-A-4-204848
Patent Document 6: WO04/074937
Non-Patent Document 1: S. A. MacDonald et al., Proc. SPIE, Vol. 1466, P2(1991)

DISCLOSURE OF THE INVENTION

1. Objects to be Accomplished by the Invention

It is an object of the present invention to provide a fluorinated compound having high concentration of functional groups and adequate characteristics of the functional groups and having high transparency in a wide wavelength region, a fluoropolymer and a process for its production. Further, it is an object of the present invention to provide, as a chemical amplification type resist, a resist composition excellent in transparency particularly for far ultraviolet rays such as KrF or ArF excimer laser or vacuum ultraviolet rays such as $F_2$ excimer laser and in dry etching characteristics, and capable of providing a resist pattern excellent in sensitivity, resolution, dissolution speed, flatness and the like. Further, it is an object of the present invention to provide a composition for a resist protective film to protect the resist film from a liquid immersion solvent in a process of liquid immersion lithography.

2. Means to Accomplish the Objects

In order to accomplish the objects as mentioned above, the present invention provides fluorinated dienes represented by the following formulae (1) to (3):

$$CF_2=CFCF_2C(CF_3)(OR^1)-(CH_2)_nCR^2=CHR^3 \quad (1)$$

$$CF_2=CFCH_2CHQ^1-(CH_2)_2CR^2=CHR^3 \quad (2)$$

$$CF_2=CFCH_2CHQ^2-CR^2=CHR^3 \quad (3)$$

In the above formula (1), $R^1$ is a hydrogen atom, an alkyl group having at most 20 carbon atoms, or $(CH_2)_aCOOR^4$ (wherein a is 0 or 1, and $R^4$ is a hydrogen atom or an alkyl group having at most 20 carbon atoms), provided that when $R^1$ or $R^4$ is an alkyl group, some or all of its hydrogen atoms may be substituted by fluorine atoms, or it may have an etheric oxygen atom, each of $R^2$ and $R^3$, which are independent of each other, is a hydrogen atom or an alkyl group having at most 12 carbon atoms, provided that when $R^2$ or $R^3$ is an alkyl group, some or all of its hydrogen atoms may be substituted by fluorine atoms, or it may have an etheric oxygen atom, and n is 0 or 2, provided that when n is 0, at least one of $R^1$, $R^2$ and $R^3$ is other than a hydrogen atom.

In the above formula (2), each of $R^2$ and $R^3$, which are independent of each other, is a hydrogen atom or an alkyl group having at most 12 carbon atoms, $Q^1$ is $(CH_2)_bC(CF_3)_c(R^5)_dOR^1$ (wherein b is an integer of from 0 to 3, c and d are integers of from 0 to 2 satisfying c+d=2, $R^5$ is a hydrogen atom or a methyl group, $R^1$ is a hydrogen atom, an alkyl group having at most 20 carbon atoms, or $(CH_2)_aCOOR^4$ (wherein a is 0 or 1, and $R^4$ is a hydrogen atom or an alkyl group having at most 20 carbon atoms), provided that when $R^1$, $R^2$, $R^3$ or $R^4$ is an alkyl group, some or all of its hydrogen atoms may be substituted by fluorine atoms, or it may have an etheric oxygen atom.

In the above formula (3), each of $R^2$ and $R^3$, which are independent of each other, is a hydrogen atom or an alkyl group having at most 12 carbon atoms, $Q^2$ is $(CH_2)_bC(CF_3)_c(R^5)_dOR^1$ (wherein b is an integer of from 0 to 3, c and d are integers of from 0 to 2 satisfying c+d=2, $R^5$ is a hydrogen atom or a methyl group, $R^1$ is a hydrogen atom, an alkyl group having at most 20 carbon atoms, or $(CH_2)_aCOOR^4$ (wherein a is 0 or 1, and $R^4$ is a hydrogen atom or an alkyl group having at most 20 carbon atoms), provided that when $R^1$, $R^2$, $R^3$ or $R^4$ is an alkyl group, some or all of its hydrogen atoms may be substituted by fluorine atoms, or it may have an etheric oxygen atom, and provided that when b is 1, d is 1 or 2, or at least one of $R^2$ and $R^3$ is an alkyl group having at most 12 carbon atoms.

Further, the present invention provides a fluoropolymer having monomer units formed by cyclopolymerization of the fluorinated diene represented by any one of the above formulae (1) to (3).

Further, the present invention provides a process for producing a fluoropolymer, characterized by cyclopolymerization of the fluorinated diene represented by any one of the above formulae (1) to (3).

Further, the present invention provides a resist composition characterized by comprising a fluoropolymer having monomer units formed by cyclopolymerization of a fluorinated diene represented by any one of the above formulae (1) to (3), an acid-generating compound which generates an acid when irradiated with light, and an organic solvent.

Further, the present invention provides a composition for a resist protective film, characterized by comprising a fluoropolymer having monomer units formed by cyclopolymerization of a fluorinated diene represented by the following formula (14) or a fluorinated diene represented by the following formula (15), and a solvent for dissolving the fluoropolymer:

$$CF_2=CFCF_2C(CF_3)(OR^1)-(CH_2)_nCR^2=CHR^3 \quad (14)$$

$$CF_2=CFCH_2CHQ-(CH_2)_nCR^2=CHR^3 \quad (15)$$

In the above formula (14), $R^1$ is a hydrogen atom, an alkyl group having at most 20 carbon atoms, or $(CH_2)_aCOOR^4$ (wherein a is 0 or 1, and $R^4$ is a hydrogen atom or an alkyl group having at most 20 carbon atoms), provided that when $R^1$ or $R^4$ is an alkyl group, some or all of its hydrogen atoms may be substituted by fluorine atoms, and it may have an etheric oxygen atom. Each of $R^2$ and $R^3$, which are independent of each other, is a hydrogen atom or an alkyl group having at most 12 carbon atoms, provided that when $R^2$ or $R^3$ is an alkyl group, some or all of its hydrogen atoms may be substituted by fluorine atoms, or it may have an etheric oxygen atom, and n is an integer of from 0 to 2.

In the above formula (15), each of $R^2$ and $R^3$, which are independent of each other, is a hydrogen atom or an alkyl group having at most 12 carbon atoms, Q is $(CH_2)_bC(CF_3)_c(R^5)_dOR^1$ (wherein b is an integer of from 0 to 3, c and d are integers of from 0 to 2 satisfying c+d=2, and $R^5$ is a hydrogen atom or a methyl group. $R^1$ is a hydrogen atom, an alkyl group having at most 20 carbon atoms or $(CH_2)_aCOOR^4$ (a is 0 or 1, $R^4$ is a hydrogen atom or an alkyl group having at most 20 carbon atoms) When $R^1$, $R^2$, $R^3$ or $R^4$ is an alkyl group, some or all of its hydrogen atoms may be substituted by fluorine atoms, or it may have an etheric oxygen atom, and n is an integer of from 0 to 2.

Further, the present invention provides a fluorinated copolymer having units derived from monomer units formed by cyclopolymerization of a fluorinated diene represented by the above formula (14) or the above formula (15), and units derived from monomer units formed by polymerization of a vinyl ester monomer represented by the following formula (16):

$$CH_2=CHOC(O)R^8 \quad (16)$$

In the above formula (16), $R^8$ is an alkyl group having at most 8 carbon atoms.

In the above fluorinated copolymer, the fluorinated diene represented by the above formula (14) is preferably a fluorinated diene represented by the following formula (14-1):

$$CF_2=CFCF_2C(CF_3)(OH)-(CH_2)_nCR^2=CHR^3 \quad (14-1)$$

wherein $R^2$, $R^3$ and n is the same as in formula (14).

The fluorinated diene represented by the above formula (14-1) is more preferably a fluorinated diene represented by the following formula (14-1-1) or (14-1-2):

$$CF_2=CFCF_2C(CF_3)(OH)-CH=CH_2 \quad (14-1-1)$$

$$CF_2=CFCF_2C(CF_3)(OH)-CH_2CH=CH_2 \quad (14-1-2)$$

In the above fluorinated copolymer, the fluorinated diene represented by the above formula (15) is preferably a fluorinated diene represented by the following formula (15-1):

$$CF_2=CFCH_2CH(C(CF_3)_2(OH))(CH_2)_nCR^2=CHR^3 \quad (15-1)$$

wherein $R^2$, $R^3$ and n are the same as in formula (14).

The fluorinated diene represented by the above formula (15-1) is more preferably a fluorinated diene represented by the following formula (15-1-1):

$$CF_2=CFCH_2CH(C(CF_3)_2(OH))CH_2CH=CH_2 \quad (15-1-1)$$

In the above fluorinated copolymer, the vinyl ester monomer represented by the above formula (16) is preferably a vinyl ester monomer represented by the following formula (16-1) or (16-2):

Further, the present invention provides a process for producing a fluorinated copolymer, characterized by copolymerizing a fluorinated diene represented by the above formula (14) or the above formula (15) and a vinyl ester monomer represented by the above formula (16).

Further, the present invention provides a composition for a resist protective film, which comprises the above fluorinated copolymer, and a solvent for dissolving the fluorinated copolymer.

Further, the present invention provides a process for forming a resist pattern, which comprises forming a resist film on one main surface of a substrate, forming on said resist film a resist protective film by means of the composition for the above resist protective film, subjecting the substrate having said resist film and said resist protective film formed thereon to exposure by immersion lithography, followed by development by means of an alkaline developer.

3. Effect of the Invention

According to the present invention, it is possible to produce a fluoropolymer having an alicyclic structure in its main chain and having functional groups in its side chains. The fluoropolymer obtained by the present invention has high chemical stability and heat resistance. Yet, functional groups are introduced in the side chains, whereby it is possible to exhibit sufficient characteristics of functional groups without bringing about a decrease of Tg, which used to be difficult to accomplish with conventional fluoropolymers. Further, such a fluoropolymer has high transparency in a wide wavelength region.

The resist composition of the present invention can be used as a chemical amplification type resist excellent particularly in transparency for far ultraviolet rays such as KrF or ArF excimer laser or vacuum ultraviolet rays such as $F^2$ excimer laser and in dry etching characteristics, and can readily form a resist pattern excellent in sensitivity, resolution, flatness, heat resistance and the like.

The composition for a resist protective film of the present invention is particularly useful for a process of liquid immersion lithography. Namely, the composition for a resist protective film of the present invention is insoluble in a liquid immersion solvent to be used in the liquid immersion lithography process, and is soluble in an alkaline developer to be used in said step.

Accordingly, by using the composition for a resist protective film of the present invention, it is possible to prevent the resist film from swelling, and further prevent contamination of a lens by dissolution of the resist film.

BEST MODE FOR CARRYING OUT THE INVENTION

By the present invention, it has been made possible to produce cyclized fluoropolymers having functional groups in side chains of the cyclic structure.

Namely, by the present invention, it is possible to obtain fluoropolymers having monomer units formed by cyclopolymerization of the fluorinated dienes represented by the following formulae (1) to (3) (hereinafter respectively referred to as fluorinated diene (1), fluorinated diene (2) and fluorinated diene (3) of the present invention).

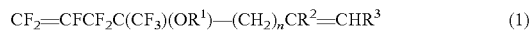

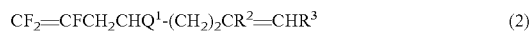

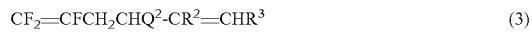

In the above formula (1), $R^1$ is a hydrogen atom, an alkyl group having at most 20 carbon atoms, or $(CH_2)_a COOR^4$ (wherein a is 0 or 1, and $R^4$ is a hydrogen atom or an alkyl group having at most 20 carbon atoms), provided that when $R^1$ or $R^4$ is an alkyl group, some or all of its hydrogen atoms may be substituted by fluorine atoms, or it may have an etheric oxygen atom, each of $R^2$ and $R^3$, which are independent of each other, is a hydrogen atom or an alkyl group having at most 12 carbon atoms, provided that when $R^2$ or $R^3$ is an alkyl group, some or all of its hydrogen atoms may be substituted by fluorine atoms, or it may have an etheric oxygen atom, and n is 0 or 2, provided that when n is 0, at least one of $R^1$, $R^2$ and $R^3$ is other than a hydrogen atom.

In the above formula (2), each of $R^2$ and $R^3$, which are independent of each other, is a hydrogen atom or an alkyl group having at most 12 carbon atoms, $Q^1$ is $(CH_2)_b C(CF_3)_c (R^5)_d OR^1$ (wherein b is an integer of from 0 to 3, c and d are integers of from 0 to 2 satisfying c+d=2, $R^5$ is a hydrogen atom or a methyl group, $R^1$ is a hydrogen atom, an alkyl group having at most 20 carbon atoms, or $(CH_2)_a COOR^4$ (wherein a is 0 or 1, and $R^4$ is a hydrogen atom or an alkyl group having at most 20 carbon atoms), provided that when $R^1$, $R^2$, $R^3$ or $R^4$ is an alkyl group, some or all of its hydrogen atoms may be substituted by fluorine atoms, or it may have an etheric oxygen atom.

In the above formula (3), each of $R^2$ and $R^3$, which are independent of each other, is a hydrogen atom or an alkyl group having at most 12 carbon atoms, $Q^2$ is $(CH_2)_b C(CF_3)_c (R^5)_d OR^1$ (wherein b is an integer of from 0 to 3, c and d are integers of from 0 to 2 satisfying c+d=2, $R^5$ is a hydrogen atom or a methyl group, $R^1$ is a hydrogen atom, an alkyl group having at most 20 carbon atoms, or $(CH_2)_a COOR^4$ (wherein a is 0 or 1, and $R^4$ is a hydrogen atom or an alkyl group having at most 20 carbon atoms), provided that when $R^1$, $R^2$, $R^3$ or $R^4$ is an alkyl group, some or all of its hydrogen atoms may be substituted by fluorine atoms, or it may have an etheric oxygen atom, and provided that when b is 1, d is 1 or 2, or at least one of $R^2$ and $R^3$ is an alkyl group having at most 12 carbon atoms.

In the fluorinated dienes (1) to (3), each of $R^2$ and $R^3$, which are independent of each other, is a hydrogen atom or an alkyl group having at most 12 carbon atoms. The alkyl group having at most 12 carbon atoms may have not only a straight or branched aliphatic hydrocarbon but also an alicyclic hydrocarbon group. In the alkyl group having at most 12 carbon atoms, some or all of its hydrogen atoms may be substituted by fluorine atoms, or it may have an etheric oxygen atom.

The alicyclic hydrocarbon group is preferably a hydrocarbon group having at least one cyclic structure, and it includes, for example, the following monocyclic saturated hydrocarbon groups, such as a cyclobutyl group, a cycloheptyl group and a cyclohexyl group, bicyclic saturated hydrocarbon groups such as a 4-cyclohexylcyclohexyl group, polycyclic saturated hydrocarbon groups such as 1-decahydronaphthyl group and 2-decahydronaphthyl group, crosslinked cyclic saturated hydrocarbon groups such as a 1-norbornyl group and a 1-adamantyl group, and spirohydrocarbon groups such as a spiro[3,4]octyl group:

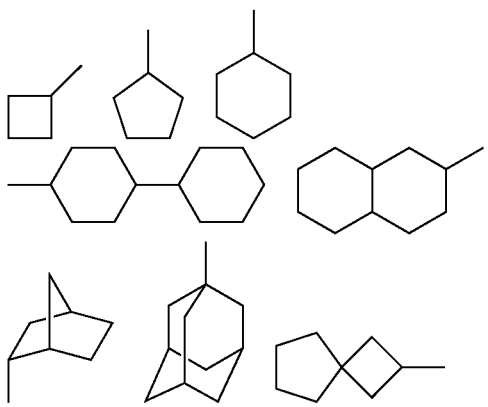

Each of the above $R^2$ and $R^3$ is preferably a hydrogen atom, a methyl group, a trifluoromethyl group or an alicyclic hydrocarbon group having at most 6 carbon atoms, particularly preferably a hydrogen atom or a methyl group. Both $R^2$ and $R^3$ are most preferably hydrogen atoms. However, in the fluorinated diene (1), when both $R^2$ and $R^3$ are hydrogen atoms and n is 0, $R^1$ is not a hydrogen atom. Further, in the fluorinated diene (3), when both $R^2$ and $R^3$ are hydrogen atoms and b is 1, d is 1 or 2.

In the fluorinated diene (2), $Q^1$ is $(CH_2)_bC(CF_3)_c(R^5)_dOR^1$. Here, b is an integer of from 0 to 3, c and d are integers of from 0 to 2 satisfying c+d=2, and $R^5$ is a hydrogen atom or a methyl group. Here, b is preferably 0 or 1, since the solubility in a basic developer will be good when a fluoropolymer obtained by cyclopolymerization of the fluorinated diene (2) is used as the after-mentioned resist composition or composition for a resist protective film. Further, b is particularly preferably 0, since the solubility in the basic developer will be better.

In the fluorinated diene (3), $Q^2$ is $(CH_2)_bC(CF_3)_c(R^5)_dOR^1$. Here, b is an integer of from 0 to 3, c and d are integers of from 0 to 2 satisfying c+d=2, and $R^5$ is a hydrogen atom or a methyl group. Here, b is preferably 0, since the solubility in the basic developer will be good when a fluoropolymer obtained by cyclopolymerization of the fluorinated diene (3) is used as the after-mentioned resist composition or composition for a resist protective film. Further, it is particularly preferred that b is 0 and c is 2, since the solubility in the basic developer will be better.

In the fluorinated dienes (1) to (3), $R^1$ is an alkyl group having at most 20 carbon atoms, or $(CH_2)_aCOOR^4$, (wherein a is 0 or 1, and $R^4$ is a hydrogen atom or an alkyl group having at most 20 carbon atoms). When $R^1$ or $R^4$ is an alkyl group, some or all of its hydrogen atoms may be substituted by fluorine atoms, or it may have an etheric oxygen atom.

The alkyl group having at most 20 carbon atoms may have not only a straight or branched aliphatic hydrocarbon group but also an alicyclic hydrocarbon group. As the alicyclic hydrocarbon group, the same group as mentioned above may be used, or may have an etheric oxygen atom in its cyclic structure.

Its specific examples may be a methyl group, a trifluoromethyl group, $CH_2OC_4H_9$-t, $CH_2OC_2H_5$, $CH_2OCH_2CF_3$, a 2-tetrahydropyranyl group and the following groups (in order to make clear their bonding position, they are shown in the form of —$OR^1$).

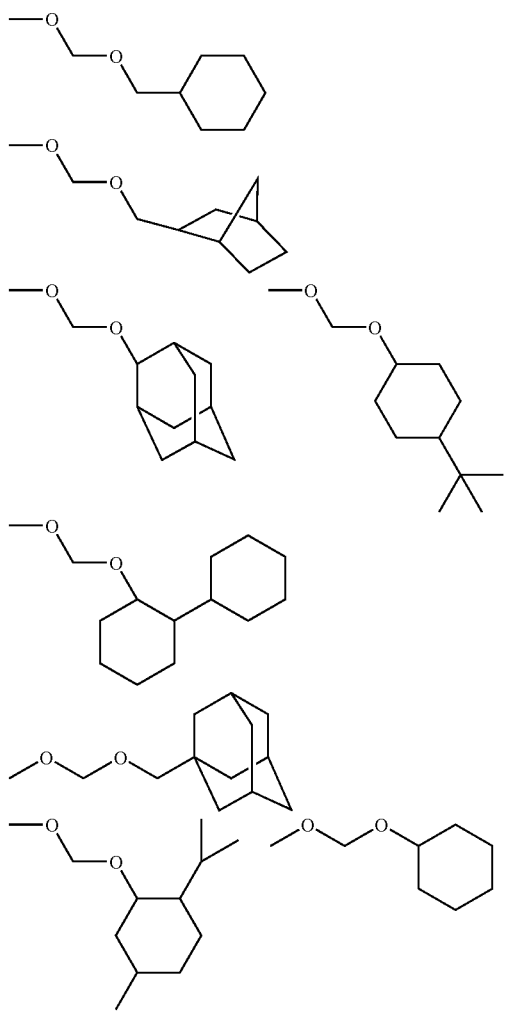

Specific examples of the above $(CH_2)_aCOOR^4$ may be $COO(t-C_4H_9)$ and $CH_2COO(t-C_4H_9)$.

When the above $R^4$ is an alkyl group having at most 20 carbon atoms, the alkyl group may have an alicyclic hydrocarbon group, and preferably has at most 12 carbon atoms. As the alicyclic hydrocarbon group, the same group as mentioned above may be used, and the following groups may specifically be mentioned (in order to make clear their bonding position, they are shown in the form of —$OR^4$).

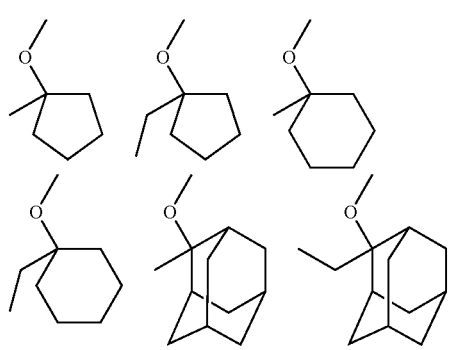

-continued

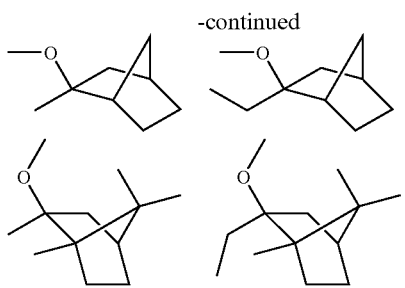

$R^4$ is preferably a hydrogen atom or an alkyl group having at most 4 carbon atoms, particularly preferably a hydrogen atom or a t-butyl group.

In the fluorinated diene (1), each of $R^2$ and $R^3$, which are independent of each other, is preferably a hydrogen atom or an alicyclic hydrocarbon group having at most 6 carbon atoms, and $R^1$ is preferably a hydrogen atom, an alkyl group having at most 20 carbon atoms or $(CH_2)_aCOOR^4$ (wherein a is 0 or 1, and $R^4$ is a hydrogen atom or an alkyl group having at most 20 carbon atoms).

However, when n is 0, all of $R^1$, $R^2$ and $R^3$ are not hydrogen atoms.

When $R^1$, $R^2$, $R^3$ or $R^4$ is an alkyl group, some or all of its hydrogen atoms may be substituted by fluorine atoms, or it may have an etheric oxygen atom.

The fluorinated diene (1) is more preferably a fluorinated diene represented by the following formula (5) or the following formula (6):

$$CF_2=CFCF_2C(CF_3)(OR^1)-CH=CH_2 \qquad (5)$$

$$CF_2=CFCF_2C(CF_3)(OR^1)-(CH_2)_2CH=CH_2 \qquad (6)$$

In the formulae, $R^1$ is as defined above.

The fluorinated diene (1) is more preferably a fluorinated diene represented by the following formula (7):

$$CF_2=CFCF_2C(CF_3)(OH)-(CH_2)_2CH=CH_2 \qquad (7)$$

In the fluorinated diene (2), each of $R^2$ and $R^3$, which are independent of each other, is preferably a hydrogen atom or an alicyclic hydrocarbon group having at most 6 carbon atoms, and $Q^1$ is preferably $(CH_2)_bC(CF_3)_c(R^5)_dOR^1$ (wherein b is an integer of from 0 to 3, c and d are integers of from 0 to 2 satisfying c+d=2, $R^5$ is a hydrogen atom or a methyl group, $R^1$ is a hydrogen atom, an alkyl group having at most 20 carbon atoms, or $(CH_2)_aCOOR^4$ (wherein a is 0 or 1, $R^4$ is a hydrogen atom or an alkyl group having at most 20 carbon atoms).

In the fluorinated diene (3), each of $R^2$ and $R^3$, which are independent of each other, is preferably a hydrogen atom or an alicyclic hydrocarbon group having at most 6 carbon atoms, and $Q^2$ is preferably $(CH_2)_bC(CF_3)_c(R^5)_dOR^1$ (wherein b is an integer of from 0 to 3, c and d are integers of from 0 to 2 satisfying c+d=2, $R^5$ is a hydrogen atom or a methyl group, $R^1$ is a hydrogen atom, an alkyl group having at most 20 carbon atoms, or $(CH_2)_aCOOR^4$ (wherein a is 0 or 1, and $R^4$ is a hydrogen atom or an alkyl group having at most 20 carbon atoms). Further, it is preferred that b is 0, since the solubility in the basic developer will be good when the fluoropolymer obtained by cyclopolymerization of the fluorinated diene (3) is used as the after-mentioned resist composition or composition for a resist protective film, and it is particularly preferred that b is 0 and c is 2. When b is 0 and c is 2, the acidity of the terminal hydroxyl group in $Q^2$ becomes high, whereby the solubility in the basic developer becomes higher. Further, when the fluoropolymer obtained by cyclopolymerization of the fluorinated diene (3) is used as the after-mentioned resist composition or composition for a resist protective film, from the viewpoint of high transparency, $R^1$ is preferably an alkyl group having at most 20 carbon atoms having no carbonyl group, and further, it is particularly preferred that as a blocking group for a hydroxyl group, a methyleneoxy($-CH_2O-$) group is bonded to the oxygen atom so that it can readily be eliminated by an acid.

Further, when $R^1$, $R^2$, $R^3$ or $R^4$ is an alkyl group, some or all of its hydrogen atoms may be substituted by fluorine atoms, or it may have an etheric oxygen atom.

The fluorinated diene (2) is preferably a fluorinated diene represented by the following formula (8) or (9):

$$CF_2=CFCH_2CH(C(CF_3)_2OR^1)-(CH_2)_2CH=CH_2 \qquad (8)$$

$$CF_2=CFCH_2CH(CH_2C(CF_3)_2OR^1)-(CH_2)_2CH=CH_2 \qquad (9)$$

In the formulae, $R^1$ is as defined above. The fluorinated diene (2) is more preferably a fluorinated diene represented by the formula (10):

$$CF_2=CFCH_2CHQ^3-(CH_2)_2CH=CH_2 \qquad (10)$$

In the above formula (10), $Q^3$ is $(CH_2)_eC(CF_3)_2OH$ (wherein e is 0 or 1).

The fluorinated diene (3) is preferably a fluorinated diene represented by the following formula (11) or (12). In the formulae, $R^1$ is as defined above, provided that in the case of the fluorinated diene of the following formula (12), $R^1$ is other than a hydrogen atom.

$$CF_2=CFCH_2CH(C(CF_3)_2OR^1)-CH=CH_2 \qquad (11)$$

$$CF_2=CFCH_2CH(CH_2C(CF_3)_2OR^1)-CH=CH_2 \qquad (12)$$

The fluorinated diene (3) is more preferably a fluorinated diene represented by the formula (13):

$$CF_2=CFCH_2CHC(CF_3)_2(OH)CH=CH_2 \qquad (13)$$

As specific examples of the fluorinated dienes (1) to (3) of the present invention, the following may be mentioned, but they are not limited thereto.

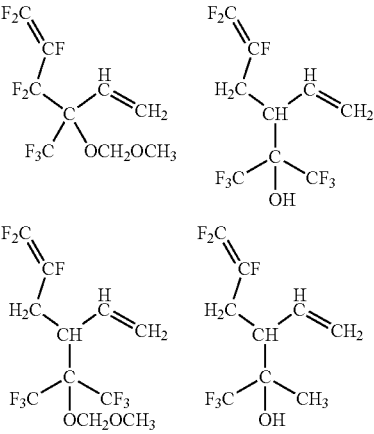

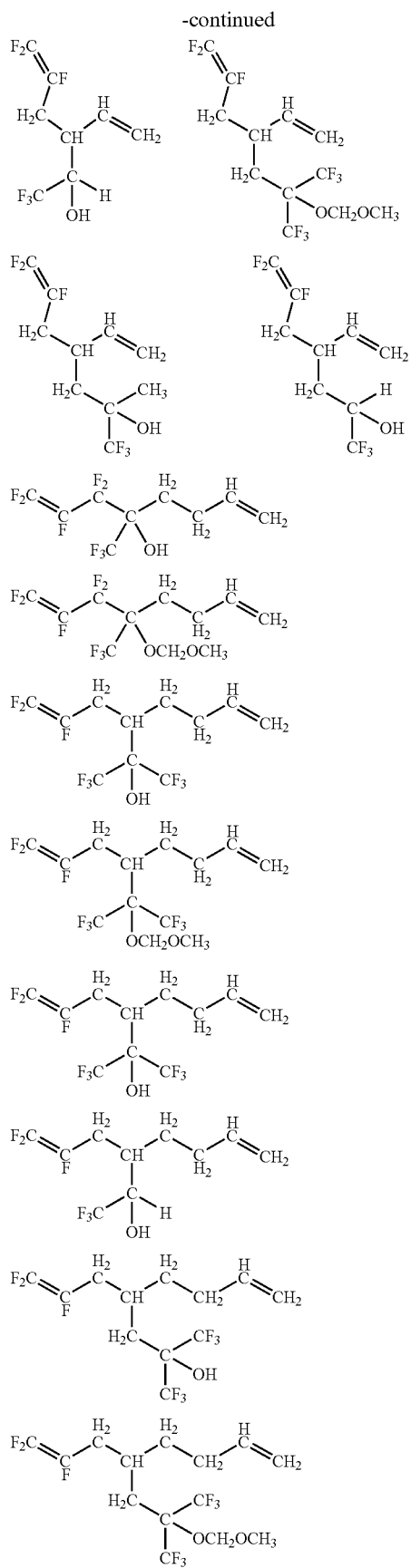
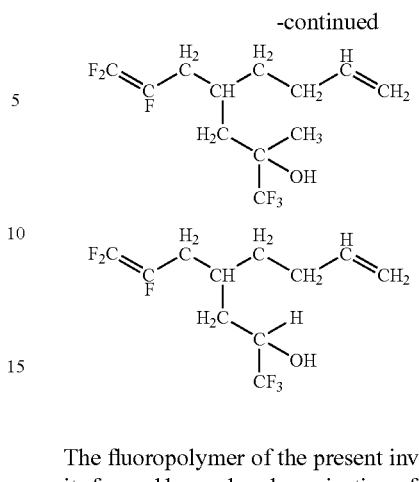

The fluoropolymer of the present invention has monomer units formed by cyclopolymerization of any one of the above fluorinated dienes (1) to (3) of the present invention. Hereinafter, a fluoropolymer having monomer units formed by cyclopolymerization of the fluorinated diene (1) will be referred to as a fluoropolymer (A), a fluoropolymer having monomer units formed by cyclopolymerization of the fluorinated diene (2) will be referred to as a fluoropolymer (B), and a fluoropolymer having monomer units formed by cyclopolymerization of the fluorinated diene (3) will be referred to as a fluoropolymer (C).

In the fluoropolymers (A) to (C) of the present invention, by the cyclopolymerization of any one of the fluorinated dienes (1) to (3), the following monomer units (a) to (f) are considered to be formed.

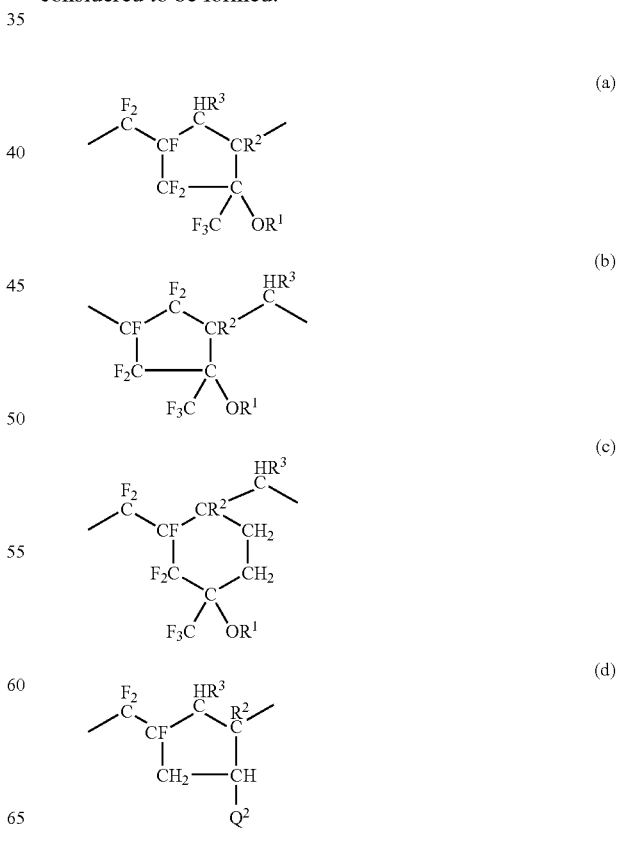

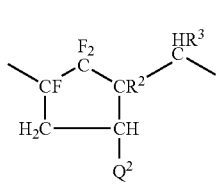

(e)

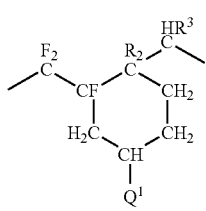

(f)

From the results of the spectroscopic analyses, etc., when n=0 in the fluorinated diene (1), the fluoropolymer (A) is considered to be a polymer having a structure comprising monomer units (a) or monomer units (b). On the other hand, when n=2 in the fluorinated diene (1), the fluoropolymer (A) is considered to be a polymer having a structure comprising monomer units (c).

The fluoropolymer (B) is considered to be a polymer having a structure comprising monomer units (f).

The fluoropolymer (C) is considered to be a polymer having a structure comprising monomer units (d) or monomer units (e).

Further, in the polymer having a structure comprising the above monomer units (a) to (f), the main chain is meant for a carbon chain constituted by four carbon atoms which constitute polymerizable unsaturated bonds.

In the fluoropolymer of the present invention, when $OR^1$ is an acidic group as in a case where $R^1$ is a hydroxyl group, the acidic group may be blocked by reacting it with a blocking agent such as an alcohol, a carboxylic acid or an active derivative thereof. Further, in a case where the fluoropolymer is to be used for a resist composition as mentioned below, it is rather preferred that the $OR^1$ group as an acidic group is blocked. Here, the active derivative may, for example, be an alkyl halide, an acid chloride, an acid anhydride, a chlorcarbonate, a dialkyl dicarbonate (such as di-tert-butyl dicarbonate) or 3,4-dihydro-2H-pyran.

As specific examples of $R^1$ as a blocked acidic group, a methoxymethyl group, an ethoxymethyl group, a 2-methoxyethoxymethyl group, $COO(t-C_4H_9)$, $CH(CH_3)OC_2H_5$, a 2-tetrahydropyranyl group and the following groups may be mentioned.

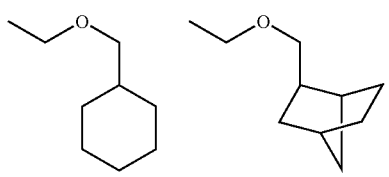

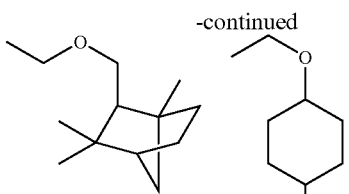

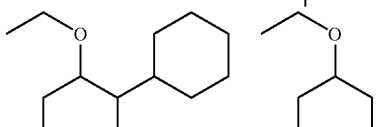

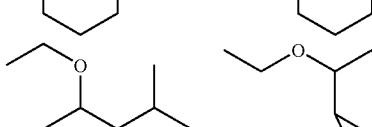

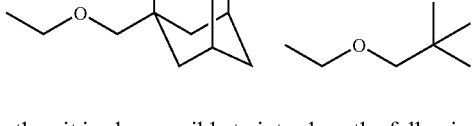

Further, it is also possible to introduce the following huge blocked acidic group having at least 20 carbon atoms.

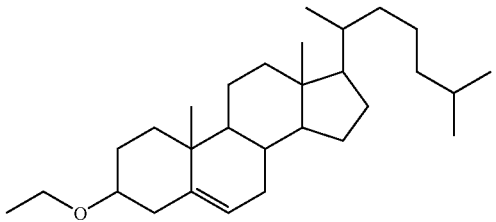

Specific examples of the reagent useful as a blocking agent are disclosed in Handbook of Reagents for Organic Synthesis: Activating Agents and Protecting Groups, compiled by A. J. Pearson and W. R. Roush, published by John Wiley & Sons (1999).

In a case where the fluoropolymer of the present invention is to be used for a resist composition as mentioned below, it is preferred that the acidic group $OR^1$ is blocked to such a degree that the unexposed portion will not be dissolved by a developer. In such a case, the blocked proportion of the acidic groups $OR^1$ (the proportion of the blocked $OR^1$ based on the total number of the acidic groups $OR^1$) is preferably from 10 to 100 mol %, particularly preferably from 10 to 50 mol %.

The fluoropolymer (A) of the present invention contains monomer units formed by cyclopolymerization of the fluorinated diene (1) as essential components, the fluoropolymer (B) contains monomer units formed by cyclopolymerization of the fluorinated diene (2) as essential components, and the fluoropolymer (C) contains monomer units formed by cyclopolymerization of the fluorinated diene (3) as essential components, but may further contain monomer units derived from other radical polymerizable monomers (hereinafter referred to as other monomers) within a range not to impair the characteristics. The proportion of such other monomer units is preferably at most 50 mol %, particularly preferably at most 15 mol %.

Such other monomers may, for example, be an α-olefin such as ethylene, propylene or isobutylene, a fluorinated olefin such as tetrafluoroethylene or hexafluoropropylene, a fluorinated cyclic monomer such as perfluoro(2,2-dimethyl-1,3-dioxol), a cyclopolymerizable perfluorodiene or hydrofluorodiene, such as perfluoro(butenyl vinyl ether), an acryl ester such as methyl acrylate or ethyl methacrylate, a vinyl ester having a cyclic structure, such as vinyl benzoate or vinyl adamantate, a vinyl ether such as ethyl vinyl ether or cyclohexyl vinyl ether, a cyclic olefin such as cyclohexene, norbornene or norbornadiene, maleic anhydride, or vinyl chloride.

Further, a monomer having a blocked acidic group may also supplementarily be used. As such a monomer, a (meth)acrylate such as tetrahydropyranyl acrylate, a vinyl ether such as tert-butyl vinyl ether, $CH_2=CHCH_2C(CF_3)_2OCO_2$-t-$C_4H_9$, $CH_2=CHCH_2C(CF_3)_2OCH(CH_3)OC_2H_5$ may, for example, be mentioned.

Among them, the following hydrofluorodienes, acrylates, and methacrylates are preferred:

$CF_2=CFCF_2$—$C(CF_3)(OH)$—$CH_2CH=CH_2$ $CF_2=CFCF_2$—$C(CF_3)(OCH_2OCH_3)$—$CH_2CH=CH_2$ $CF_2=CFCH_2$—$CH(CH_2C(CF_3)_2OH)$—$CH_2CH=CH_2$ $CF_2=CFCH_2$—$CH(CH_2C(CF_3)_2OCH_2OCH_3)$—$CH_2CH=CH_2$ $CF_2=CFCH_2$—$CH(C(CF_3)_2OH)$—$CH_2CH=CH_2$ $CF_2=CFCH_2$—$CH(C(CF_3)_2OCH_2OCH_3)$—$CH_2CH=CH_2$ $CH_2=CHC(O)OR$ $CH_2=C(CH_3)C(O)OR$ $CH_2=CFC(O)OR$ $CH_2=C(CF_3)C(O)OR$

Here, in the above formulae, as specific examples of OR groups, the following groups may be mentioned.

$OC(CH_3)_3$, $OCH(CF_3)_2$

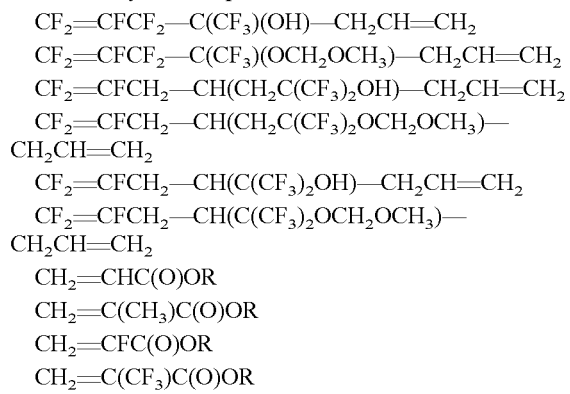

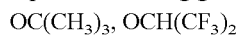

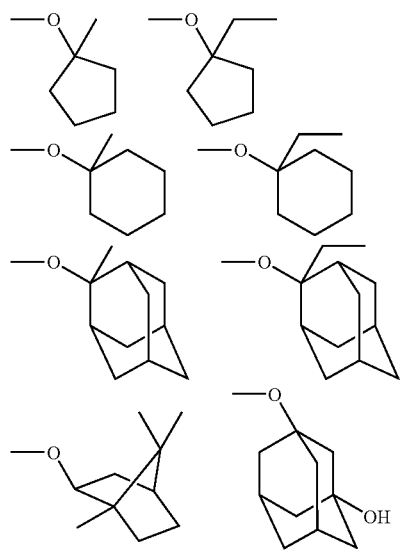

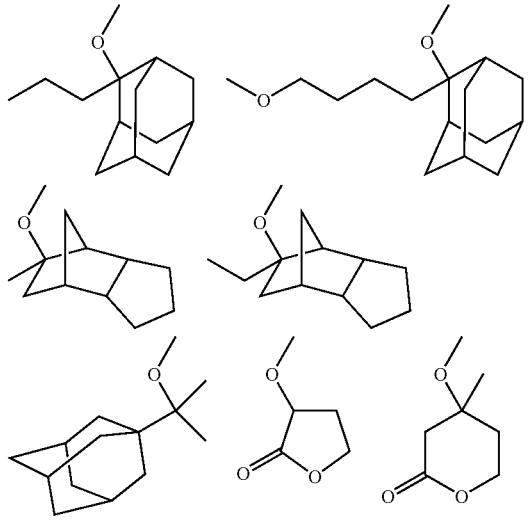

The molecular weight of the fluoropolymer of the present invention may suitably be selected depending upon the particular application. For example, in a case where it is used for a resist composition as mentioned below, it is required to be uniformly dissolved in an organic solvent and uniformly applied on a substrate, and therefore, usually, its number average molecular weight as calculated as polystyrene is suitably from 1,000 to 100,000, preferably from 2,000 to 20,000. If the number average molecular weight is less than 1,000, a trouble is likely to result such that the obtainable resist pattern tends to be poor, the film remaining rate after development tends to be low, or the dimensional stability during the heat treatment of the pattern tends to deteriorate. On the other hand, if the number average molecular weight exceeds 100,000, the coating property of the composition is likely to be poor, or the developability may deteriorate. Further, in the case of using the fluoropolymer for a composition for a resist protective film as mentioned below, its number average molecular weight as calculated as polystyrene is suitably from 1,000 to 100,000, preferably from 2,000 to 20,000.

The fluoropolymer (A) of the present invention can be obtained by cyclopolymerization of the fluorinated diene (1) in the presence of a polymerization initiator. The fluoropolymer (B) of the present invention can be obtained by cyclopolymerization of the fluorinated diene (2) in the presence of a polymerization initiator. The fluoropolymer (C) of the present invention can be obtained by cyclopolymerization of the fluorinated diene (3) in the presence of a polymerization initiator. In the present specification, the expression "cyclopolymerization" includes, other than cyclopolymerization of one type of the fluorinated dienes (1) to (3) of the present invention to obtain a homopolymer, cyclopolymerization of two or more fluorinated dienes (1) and further copolymerization thereof to obtain a copolymer, cyclopolymerization of two or more fluorinated dienes (2) and further copolymerization thereof to obtain a copolymer, cyclopolymerization of two or more fluorinated dienes (3) and further copolymerization thereof to obtain a copolymer, and cyclopolymerization of any of the fluorinated dienes (1) to (3) of the present invention and further copolymerization thereof with the above other monomers to obtain a copolymer having other monomer units as repeating units. Further, the expression also includes cyclopolymerization of at least two of the fluorinated dienes (1) to (3) and further copolymerization thereof to obtain a copolymer, and further copolymerization of such a copolymer and other monomers to obtain a copolymer.

The polymerization initiating source is not particularly limited so long as it is capable of letting the polymerization reaction proceed radically, and it may, for example, be a radical-generating agent, light or ionizing radiation. A radical-generating agent is particularly preferred, and it may, for example, be a peroxide, an azo compound or a persulfate. Among them, the following peroxides are preferred.

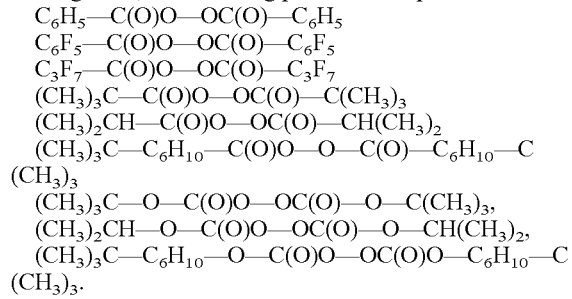

$C_6H_5$—C(O)O—OC(O)—$C_6H_5$
$C_6F_5$—C(O)O—OC(O)—$C_6F_5$
$C_3F_7$—C(O)O—OC(O)—$C_3F_7$
$(CH_3)_3C$—C(O)O—OC(O)—$C(CH_3)_3$
$(CH_3)_2CH$—C(O)O—OC(O)—$CH(CH_3)_2$
$(CH_3)_3C$—$C_6H_{10}$—C(O)O—O—C(O)—$C_6H_{10}$—$C(CH_3)_3$
$(CH_3)_3C$—O—C(O)O—OC(O)—O—$C(CH_3)_3$,
$(CH_3)_2CH$—O—C(O)O—OC(O)—O—$CH(CH_3)_2$,
$(CH_3)_3C$—$C_6H_{10}$—O—C(O)O—OC(O)O—$C_6H_{10}$—$C(CH_3)_3$.

Here, $C_6H_5$ represents a phenyl group, $C_6F_5$ a pentafluorophenyl group and $C_6H_{10}$ a cyclohexylene group.

The polymerization method is also not particularly limited, and it may, for example, be so-called bulk polymerization wherein a monomer is subjected to polymerization as it is, solution polymerization which is carried out in a fluorohydrocarbon, a chlorohydrocarbon, a fluorochlorohydrocarbon, an alcohol, a hydrocarbon or other organic solvent, in which the fluorinated dienes (1) to (3) and other monomers can be dissolved or dispersed, suspension polymerization which is carried out in an aqueous medium in the absence or presence of a suitable organic solvent, or emulsion polymerization which is carried out in an aqueous medium in the presence of an emulsifier.

The organic solvent to be used as a solvent at the time of polymerization is not limited to one type, and several types of organic solvents may be used as a solvent mixture. Particularly, an aliphatic hydrocarbon such as pentane, hexane or heptane, a hydrocarbon type alcohol such as methanol, ethanol, n-propanol, isopropanol, t-butanol, a hydrocarbon type ketone such as acetone, methyl ethyl ketone, methyl isobutyl ketone or cyclohexanone, a hydrocarbon type ether such as dimethyl ether, diethyl ether, methyl ethyl ether, methyl t-butyl ether, diethylene glycol dimethyl ether or tetraethylene glycol dimethyl ether, an alicyclic hydrocarbon type ether such as tetrahydrofuran or 1,4-dioxane, a nitrile such as acetonitrile, a hydrocarbon type ester such as methyl acetate, ethyl acetate, propyl acetate, isopropyl acetate, butyl acetate, t-butyl acetate, methyl propionate or ethyl propionate, an aromatic hydrocarbon such as toluene or xylene, chlorohydrocarbon such as methylene chloride, chloroform or carbon tetrachloride, fluorochlorohydrocarbon such as R-113, R-113a, R-141b, R-225ca or R-225cb, a fluorohydrocarbon such as 1,1,1,2,2,3,3,4,4,5,5,6,6-tridecafluorohexane or 1,1,1,2,2,3,3,4,4-nonafluorohexane, a fluorohydrocarbon type ether such as methyl 2,2,3,3-tetrafluoroethyl ether, or a fluorohydrocarbon alcohol such as 2,2,2-trifluoroethanol, 1,1,1,3,3,3-hexafluoroisopropanol, 2,2,3,3-tetrafluoropropanol or 2,2,3,3,4,4,5,5-octafluoropentanol may be mentioned, but such an organic solvent is not limited thereto.

The polymerization temperature and pressure are also not particularly limited, but it is preferred to properly set them taking into consideration various factors such as the boiling point of the monomer, the heating source, removal of the polymerization heat, etc. For example, suitable temperature setting can be carried out between 0° C. to 200° C., and practically suitable temperature setting can be carried out within a range of from room temperature to 100° C. Further, the polymerization pressure may be a reduced pressure or an elevated pressure, and practically, the polymerization can properly be carried out within a range of from normal pressure to about 100 atm, preferably from normal pressure to 10 atm.

In order to obtain a fluoropolymer having $OR^1$ groups as acidic groups blocked, a fluorinated diene having an $OR^1$ group not blocked may be cyclopolymerized to produce a fluoropolymer, and then the $OR^1$ groups in the fluoropolymer may be blocked by a blocking agent. Further, a fluorinated diene having an $OR^1$ group blocked preliminarily by using a blocking agent may be cyclopolymerized to obtain a fluoropolymer having the $OR^1$ groups blocked.

The present invention also provides a resist composition characterized by comprising a fluoropolymer (A) to (C), an acid-generating compound (D) which generates an acid when irradiated with light, and an organic solvent (E).

The acid-generating compound (D) which generates an acid under irradiation with light of the present invention generates an acid under irradiation with light. By the acid thus generated, blocked acidic groups which exist in the fluoropolymer (A) to (C), will be cleaved (deblocked). As a result, the exposed portions of the resist film will become readily soluble by an alkali developer, whereby a positive resist pattern will be formed by the alkali developer. As such an acid-generating compound (D) which generates an acid under irradiation with light, it is possible to employ an acid-generating compound which is commonly used for a chemical amplification type resist material. Namely, an onium salt, a halogenated compound, a diazoketone compound, a sulfone compound or a sulfonic acid compound may, for example, be mentioned.

The following compounds may be mentioned as examples of such an acid-generating compound (D). The onium salt may, for example, be an iodonium salt, a sulfonium salt, a phosphonium salt, a diazonium salt or a pyridinium salt. Specific examples of a preferred onium salt include diphenyliodonium triflate, diphenyliodoniumpyrene sulfonate, diphenyliodoniumdodecylbenzene sulfonate, bis(4-tert-butylphenyl)iodonium triflate, bis(4-tert-butylphenyl)iodonium dodecylbenzene sulfonate, triphenylsulfonium triflate, triphenylsulfonium nonanate, triphenylsulfoniumperfluorooctane sulfonate, triphenylsulfonium hexafluoroantimonate, 1-(naphthylacetomethyl)thiolanium triflate, cyclohexylmethyl(2-oxocyclohexyl)sulfonium triflate, dicyclohexyl(2-oxocyclohexyl)sulfonium triflate, dimethyl(4-hydroxynaphthyl)sulfonium tosylate, dimethyl(4-hydroxynaphthyl)sulfonium dodecylbenzene sulfonate, dimethyl(4-hydroxynaphthyl)sulfonium naphthalene sulfonate, triphenylsulfonium camphor sulfonate or (4-hydroxyphenyl) benzylmethylsulfonium toluene sulfonate.

The halogenated compound may, for example, be a haloalkyl group-containing hydrocarbon compound or a haloalkyl group-containing heterocyclic compound. Specifically, it may, for example, be a (trichloromethyl)-s-triazine derivative such as phenyl-bis(trichloromethyl)-s-triazine, methoxyphenyl-bis(trichloromethyl)-s-triazine or naphthyl-bis(trichloromethyl)-s-triazine, or 1,1-bis(4-chlorophenyl)-2,2,2-trichloroethane.

The sulfone compound may, for example, β-ketosulfone, β-sulfonylsulfone or an α-diazo compound of such a compound. Specifically, it may, for example, be 4-trisphenacylsulfone, mesitylphenacylsulfone or bis(phenylsulfonyl) methane. The sulfonic acid compound may, for example, be an alkylsulfonic acid ester, an alkylsulfonic acid imide, a haloalkylsulfonic acid ester, an arylsulfonic acid ester or an iminosulfonate. Specifically, it may, for example, be benzoine tosylate or 1,8-naphthalene dicarboxylic acid imide triflate. In the present invention, such acid-generating compounds (D) may be used alone or in combination as a mixture of two or more of them.

The organic solvent (E) in the present invention is not particularly limited so long as it can sufficiently dissolve the fluoropolymer (A) to (C) and the acid-generating compound (D), and further, its solution can form a uniform coating film when applied by means of spin coating, cast coating, roll coating or the like.

Specific examples of the organic solvent (E) include an alcohol such as methyl alcohol, ethyl alcohol or diacetone alcohol, a ketone such as acetone, methyl isobutyl ketone, cyclohexanone, cyclopentanone, 2-heptanone, N-methyl pyrrolidone or γ-butyrolactone, an ester such as propylene glycol monomethyl ether acetate, propylene glycol monomethyl ether propionate, propylene glycol monomethyl ether acetate, carbitol acetate, methyl 3-methoxypropionate, ethyl 3-ethoxypropionate, methyl β-methoxyisobutyrate, ethyl butyrate, propyl butyrate, methyl isobutyl ketone, ethyl acetate, 2-ethoxyethyl acetate, 2-ethoxyethyl acetate, isoamyl acetate, methyl lactate or ethyl lactate, an aromatic hydrocarbon such as toluene or xylene, a glycol mono- or di-alkyl ether such as propylene glycol monomethyl ether, propylene glycol monoethyl ether, ethylene glycol monoisopropyl ether, diethylene glycol monomethyl ether, diethylene glycol dimethyl ether or propylene glycol monomethyl ether, N,N-dimethylformamide, and N,N-dimethylacetamide.

As the organic solvent, those exemplified above may be used alone or in combination of two or more of them. The moisture contained in the organic solvent is influential over the solubility of each component in the resist composition, the coating property to a substrate to be treated, the storage stability and the like. Thus, it is preferred that the amount of moisture is small.

The proportions of the respective components in the resist composition of the present invention are usually such that the acid-generating compound (D) is from 0.1 to 20 parts by mass and the organic solvent (E) is from 50 to 2,000 parts by mass, per 100 parts by mass of the fluoropolymer (A) to (C). Preferably, the acid-generating compound (D) is from 0.1 to 10 parts by mass and the organic solvent (E) is from 100 to 1,000 parts by mass, per 100 parts by mass of the fluoropolymer (A) to (C).

If the amount of the acid-generating compound (D) is at least 0.1 part by mass, sufficient sensitivity and developability can be provided, and if it is at most 10 parts by mass, sufficient transparency to radiation is retained, whereby a more accurate resist pattern can be obtained.

In the resist composition of the present invention, an acid-cleavable additive to improve the pattern contrast, a surfactant to improve the coating property, a nitrogen-containing basic compound to adjust the acid-generating pattern, an adhesion-assisting agent to improve the adhesion to a substrate or a storage stabilizer to enhance the storage stability of the composition, may be optionally incorporated. Further, the resist composition of the present invention is preferably employed in such a manner that the respective components are uniformly mixed, followed by filtration by means of a filter of from 0.1 to 2 μm.

The resist composition of the present invention is applied on a substrate such as a silicon wafer, followed by drying to form a resist film. As the coating method, spin coating, cast coating or roll coating may, for example, be employed.

The formed resist film will be irradiated with light through a mask having a pattern drawn thereon, followed by development treatment to form the pattern.

The light for the irradiation may, for example, be ultraviolet rays such as g-line having a wavelength of 436 nm or i-line having a wavelength of 365 nm, or far ultraviolet rays or vacuum ultraviolet rays, such as KrF excimer laser having a wavelength of 248 nm, ArF excimer laser having a wavelength of 193 nm or $F_2$ excimer laser having a wavelength of 157 nm. The resist composition of the present invention is a resist composition useful particularly for an application where ultraviolet rays having a wavelength of at most 250 nm, especially ultraviolet rays having a wavelength of at most 200 nm (such as ArF excimer laser or $F_2$ excimer laser), are used as the light source. In addition, the resist composition of the present invention is a resist composition applicable also to exposure employing so called liquid immersion technique to improve resolution by utilizing a size of the refractive index of e.g. water or an organic compound containing other fluorine atoms. The resist composition of the present invention is particularly preferably used for an application wherein $F_2$ excimer laser which can carry out finer pattern formation, is used as the light source, or an application wherein ArF excimer laser is used as the light source in combination with exposure employing the liquid immersion technique.

As the development treatment solution, various alkali aqueous solutions are employed. As such an alkali material, sodium hydroxide, potassium hydroxide, ammonium hydroxide, tetramethylammonium hydroxide or triethylamine may, for example, be mentioned.

Further, the present invention provides a composition for a resist protective film, which comprises a fluoropolymer having monomer units formed by cyclopolymerization of a fluorinated diene represented by the following formula (14) or (15), and a solvent (F) for dissolving the fluoropolymer:

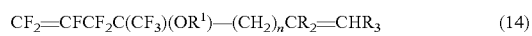

$$CF_2\!=\!CFCF_2C(CF_3)(OR^1)\!-\!(CH_2)_nCR_2\!=\!CHR_3 \quad (14)$$

$$CF_2\!=\!CFCH_2CHQ\text{-}(CH_2)_nCR_2\!=\!CHR_3 \quad (15)$$

wherein $R^1$ is a hydrogen atom, an alkyl group having at most 20 carbon atoms, or $(CH_2)_aCOOR^4$ (wherein a is 0 or 1, and $R^4$ is a hydrogen atom or an alkyl group having at most 20 carbon atoms), each of $R^2$ and $R^3$, which are independent of each other, is a hydrogen atom or an alkyl group having at most 12 carbon atoms, Q is $(CH_2)_bC(CF_3)_c(R^5)_dOR^1$ (wherein $R^1$ is as defined above, b is an integer of from 0 to 3, c and d are integers of from 0 to 2 satisfying c+d=2, and $R^5$ is a hydrogen atom or a methyl group), provided that when $R^1$, $R^2$, $R^3$ or $R^4$ is an alkyl group, some or all of its hydrogen atoms may be substituted by fluorine atoms, or it may have an etheric oxygen atom, and n is an integer of from 0 to 2.

The fluoropolymer to be used for the composition for a resist protective film of the present invention may be widely selected from the above fluoropolymers (A) to (C), and further, it may be selected from a range wider than the above description of such fluoropolymers. Particularly, in the case of the fluorinated diene (1) to constitute the fluoropolymer (A) by the cyclopolymerization, n may be 0, and all of $R^1$, $R^2$ and $R^3$ may be hydrogen atoms. Further, n may be 1. Accordingly, in the case of using it for the composition for a resist protective film of the present invention, the fluorinated diene (1) is preferably a fluorinated diene represented by the following formula (12):

$$CF_2\!=\!CFCF_2C(CF_3)(OH)\!-\!(CH_2)_nCH\!=\!CH_2 \quad (12)$$

wherein n is an integer of from 0 to 2.

Further, the above fluoropolymer (A) is made of the fluorinated diene (1) wherein n is 0 or 2, but the fluoropolymer to be used for the composition of the resist protective film of the present invention may be a fluoropolymer (hereinafter referred to also as fluoropolymer (A')) made of a fluorinated diene (hereinafter referred to also as fluorinated diene (1')) in which n is 1, in the above fluorinated diene (1).

Such a fluorinated diene (1') and the fluoropolymer (A') are all the same as the fluorinated diene (1) and the fluoropolymer (A) except that n is 1.

As a specific example of such a fluorinated diene (1'), 1,1,2,3,3-pentafluoro-4-trifluoromethyl-4-hydroxy-1,6-henpadiene[$CF_2$=$CFCF_2C(CF_3)(OH)CH_2CH$=$CH_2$], $CF_2$=$CFCF_2C(CF_3)(OCH_2COOH)CH_2CH$=$CH_2$ or $CF_2$=$CFCF_2C(CF_3)(OH)CH_2CH$=$CH(CH_3)$ may, for example, be mentioned.

The fluoropolymer to be used for the composition of the resist protective film of the present invention may be also a fluoropolymer (B') as a fluoropolymer having monomer units formed by cyclopolymerization of a fluorinated diene (2') represented by the following formula (2'):

$$CF_2=CFCH_2CHQ^1\text{-}(CH_2)CR^2=CHR^3 \quad (2')$$

(wherein each of $R^2$ and $R^3$, which are independent of each other, is a hydrogen atom or an alkyl group having at most 12 carbon atoms, $Q^1$ is $(CH_2)_bC(CF_3)_c(R^5)_dOR^1$ (wherein b is an integer of from 0 to 3, c and d are integers of from 0 to 2 satisfying c+d=2, $R^5$ is a hydrogen atom or a methyl group, $R^1$ is a hydrogen atom, an alkyl group having at most 20 carbon atoms, or $(CH_2)_aCOOR^4$ (wherein a is 0 or 1, and $R^4$ is a hydrogen atom or an alkyl group having at most 20 carbon atoms), provided that when $R^1$, $R^2$, $R^3$ or $R^4$ is an alkyl group, some or all of its hydrogen atoms may be substituted by fluorine atoms, or it may have an etheric oxygen atom).

Such a fluorinated diene (2') and the fluoropolymer (B') are cases where in the above fluorinated diene (2) and the above fluoropolymer (B), the portion of —$(CH_2)_2$— is —$(CH_2)$—, and, except for this difference, are all the same as the above fluorinated diene (2) and the above fluoropolymer (B).

As a specific example of such a fluorinated diene (2'), $CF_2$=$CFCH_2CH(C(CF_3)_2OH)CH_2CH$=$CH_2$, $CF_2$=$CFCH_2CH(C(CF_3)_2OCH_2COOH)CH_2CH$=$CH_2$ or $CF_2$=$CFCH_2CH(C(CF_3)_2OH)CH_2CH$=$CH(CH_3)$ may, for example, be mentioned.

In the case of using it for the composition for a resist protective film of the present invention, the fluorinated diene (3) to constitute the fluoropolymer (C) may be such that when b is 0, c is 2, or each of $R^2$ and $R^3$ may be a hydrogen atom. In a case where the fluoropolymer (C) is used for the resist composition, its solubility in the basic developer may be problematic, but a resist protective film is thinner than a resist film, and therefore in the case of using it for the composition for a resist protective film, the solubility in the basic developer will be sufficient.

Accordingly, in the case of using it for the composition for a resist protective film of the present invention, the fluorinated dienes (1) and (3) include the following in addition to those specifically exemplified above.

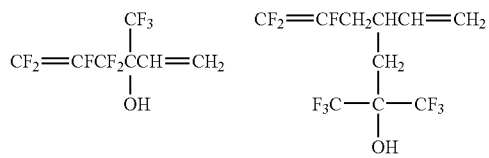

The solvent (F) in the present invention is not particularly limited so long as it is capable of dissolving a fluoropolymer which is useful for the above composition for a resist protective film of the present invention. It may, for example, be an alcohol such as methyl alcohol or ethyl alcohol, a ketone such as acetone, methyl isobutyl ketone or cyclohexanone, an acetate such as ethyl acetate or butyl acetate, an aromatic hydrocarbon such as toluene or xylene, a glycol monoalkyl ether such as propylene glycol monomethyl ether or propylene glycol monoethyl ether, or a glycol monoalkyl ether ester such as propylene glycol monomethyl ether acetate or carbitol acetate, or a fluorine type solvent, such as a flon such as fluorocarbon, hydrofluorocarbon or hydrochlorofluorocarbon, a perfluoroether, a fluoroalcohol or a fluoroketone, or a mixture thereof or a mixture of water and a water-soluble organic solvent.

The proportions of the respective components in the composition for a resist protective film of the present invention are usually such that the solvent (F) is from 50 to 10,000 parts by mass, per 100 parts by mass of the fluoropolymer. Preferably, the solvent (F) is from 100 to 1000 parts by mass, per 100 parts by mass of the fluoropolymer.

Further, the present invention provides a fluorinated copolymer to be preferably used for the composition for a resist protective film. The fluorinated copolymer of the present invention has units derived from monomer units formed by cyclopolymerization of a fluorinated diene represented by the above formula (14) or (15), and units derived from monomer units formed by polymerization of a vinyl ester monomer (hereinafter referred to as monomer (16)) represented by the following formula (16):

$$CH_2=CHOC(O)R^8 \quad (16)$$

In the formula (16), $R^8$ is an alkyl group having at most 8 carbon atoms, and is preferably a methyl group or an ethyl group.

The fluorinated diene represented by the formula (14) or (15) is as described in [0093] to [0099]. Namely, the fluorinated diene represented by the formula (14) may be, in addition to the above fluorinated diene (1), the above fluorinated diene (1) in which n is 0 and all of $R^1$, $R^2$ and $R^3$ may be hydrogen atoms. Further, the fluorinated diene represented by the formula (14) may be the above fluorinated diene (1').

However, the fluorinated diene represented by the formula (14) is preferably a fluorinated diene represented by the following formula (14-1):

$$CF_2=CFCF_2C(CF_3)(OH)\text{—}(CH_2)_nCR^2=CHR^3 \quad (14\text{-}1)$$

The fluorinated diene (14-1) is more preferably a fluorinated diene represented by the following formula (14-1-1) to (14-1-3):

$$CF_2=CFCF_2C(CF_3)(OH)\text{—}CH=CH_2 \quad (14\text{-}1\text{-}1)$$

$$CF_2=CFCF_2C(CF_3)(OH)\text{—}CH_2CH=CH_2 \quad (14\text{-}1\text{-}2)$$

$$CF_2=CFCF_2C(CF_3)(OH)\text{—}(CH_2)_2CH=CH_2 \quad (14\text{-}1\text{-}3)$$

Among them, the fluorinated diene represented by the formula (14-1-1) or (14-1-2) is particularly preferred.

On the other hand, the fluorinated diene represented by the formula (15) may be the above fluorinated diene (2') in addition to the above fluorinated diene (2). Further, in addition to the above fluorinated diene (3), the fluorinated diene represented by the formula (15) may be the above fluorinated diene (3) in which when b is 0, c is 2, or both of $R^2$ and $R^3$ are hydrogen atoms.

The fluorinated diene represented by the formula (15) is preferably a fluorinated diene represented by the following formula (15-1):

$$CF_2=CFCH_2CH(C(CF_3)_2(OH))(CH_2)_nCR^2=CHR^3 \quad (15\text{-}1)$$

The fluorinated diene represented by the formula (15) is more preferably a fluorinated diene represented by the following formula (15-1-1) to (15-2-3):

$CF_2=CFCH_2CH(C(CF_3)_2(OH))-CH=CH_2$ (15-1-1)

$CF_2=CFCH_2CH(C(CF_3)_2(OH))-CH_2CH=CH_2$ (15-1-2)

$CF_2=CFCH_2CH(C(CF_3)_2(OH))-(CH_2)_2CH=CH_2$ (15-1-3)

$CF_2=CFCH_2CH(CH_2C(CF_3)_2(OH))-CH=CH_2$ (15-2-1)

$CF_2=CFCH_2CH(CH_2C(CF_3)_2(OH))-CH_2CH=CH_2$ (15-2-2)

$CF_2=CFCH_2CH(CH_2C(CF_3)_2(OH))-(CH_2)_2CH=CH_2$ (15-2-3)

Among them, the fluorinated diene represented by the formula (15-1-1) is particularly preferred.

On the other hand, the monomer (16) is preferably a vinyl ester monomer represented by the following formula (16-1) to (16-6):

$CH_2=CHOC(O)CH_3$ (16-1)

$CH_2=CHOC(O)CH_2CH_3$ (16-2)

$CH_2=CHOC(O)CH_2CH_2CH_3$ (16-3)

$CH_2=CHOC(O)CH_2CH_2CH_2CH_3$ (16-4)

$CH_2=CHOC(O)CH_2CH_2CH_2CH_2CH_3$ (16-5)

$CH_2=CHOC(O)CH_2CH_2CH_2CH_2CH_2CH_3$ (16-6)

Among them, the vinyl ester monomer represented by the formula (16-1) or (16-2) is particularly preferred.

The fluorinated copolymer of the present invention comprises, as essential components, units derived from monomer units formed by cyclopolymerization of the fluorinated diene (14) or the fluorinated diene (15), and units derived from monomer units formed by polymerization of the monomer (16). In the fluorinated copolymer, the proportions of the monomer units formed by polymerization is of the monomer (16) is preferably at most 75 mol %, particularly preferably at most 50 mol %. When it is at most 50 mol %, the solubility in the developer will be particularly good.

In the fluorinated copolymer of the present invention, by cyclopolymerization of a suitable fluorinated diene (14-1), any of the following monomer units are considered to be produced.

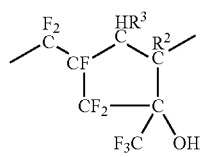
(a')

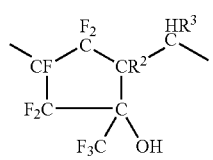
(b')

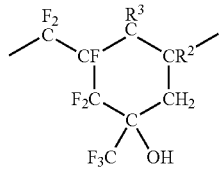
(g)

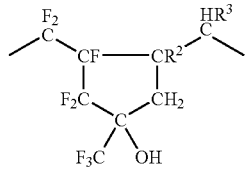
(h)

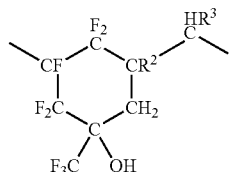
(i)

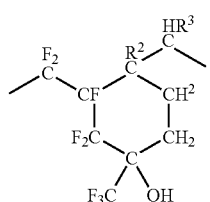
(f')

From the results of the spectroscopic analyses, etc., in the case where n is 0 in the fluorinated diene (14-1), the fluorinated copolymer is considered to be a polymer (hereinafter referred to as a copolymer (A)) having a structure containing the monomer units (a') or the monomer units (b').

In the case where n is 1 in the fluorinated diene (14-1), the fluorinated copolymer is considered to be a copolymer (hereinafter referred to as a copolymer (B)) having a structure containing the monomer units (g), the monomer units (h) or the monomer units (i).

In the case where n is 2 in the fluorinated diene (14-1), the fluorinated copolymer is considered to be a copolymer (hereinafter referred to as a copolymer (C)) having a structure containing monomer units (f').

Further, the main chain of the above copolymers (A) to (C) is meant for a carbon chain constituted by four carbon atoms which constitute polymerizable unsaturated double bonds.

In the fluorinated copolymer of the present invention, by cyclopolymerization of a suitable fluorinated diene (15-1), any of the following monomer units are considered to be produced.

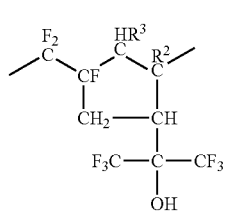
(j)

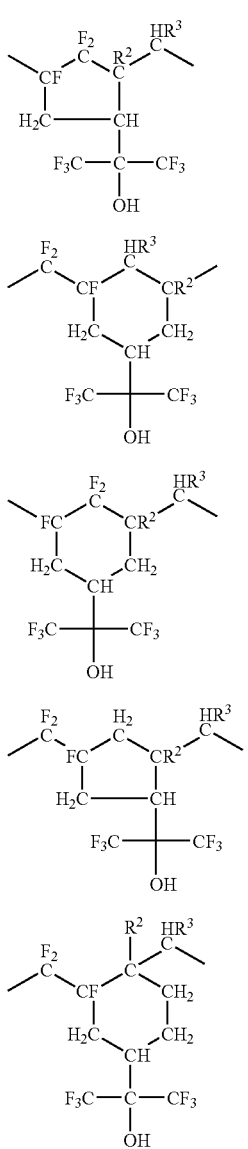

From the results of the spectroscopic analyses, etc., in the case where n is 0 in the fluorinated diene (15-1), the fluorinated copolymer is considered to be a copolymer (hereinafter referred to as a copolymer (D)) having a structure containing the monomer units (j) or the monomer units (k).

In the case where n is 1 in the fluorinated diene (15-1), the fluorinated copolymer is considered to be a copolymer (hereinafter referred to as a copolymer (E)) having a structure containing monomer units (l), monomer units (m) or monomer units (n).

In the case where n is 2 in the fluorinated diene (15-1), the fluorinated copolymer is considered to be a copolymer (hereinafter referred to as a copolymer (F)) having a structure containing the monomer units (o).

Further, the main chain of the above copolymers (D) to (F) is meant for a carbon chain constituted by carbon atoms which constitute polymerizable unsaturated double bonds.

The fluorinated copolymer containing units derived from monomer units formed by cyclopolymerization of the fluorinated diene (14) or the fluorinated diene (15), and units derived from monomer units formed by polymerization of the monomer (16) has the same levels of water-repellency (static contact angle) and solubility in the developer as the polymer (homopolymer) containing only monomer units formed by cyclopolymerization of the fluorinated diene (14) or (15). Since the monomer (16) is inexpensive as compared with the fluorinated diene (14) or (15), in the case of using the fluorinated copolymer, it is possible to obtain a composition for a resist protective film inexpensively as compared with a composition for a resist protective film using the homopolymer.

Further, by adjusting the proportion of the monomer (16), it is possible to change the acidic hydroxyl group concentration in the fluorinated copolymer, and therefore, in the case of using it for the composition for a resist protective film, it is possible to optimize the balance between the solubility in the developer and the interaction with water as a liquid immersion medium.

Further, since the units derived from the monomer units formed by polymerization of the monomer (16) have polar groups such as carbonyl groups, the composition for a resist protective film using the fluorinated copolymer is improved in the adhesion to a substrate such as a silicon wafer or a resist film, as compared with the composition for a resist protective film using the homopolymer.

The fluorinated copolymer of the present invention contains units derived from monomer units formed by cyclopolymerization of the fluorinated diene (14) or the fluorinated diene (15) and units derived from monomer units formed by polymerization of the monomer (16), as essential components, but such a copolymer may further contain monomer units derived from other radical polymerizable monomers (hereinafter referred to as other monomers) within a range not to impair the characteristics. The proportion of such other monomer units is preferably at most 50 mol %, particularly preferably at most 15 mol %. As such other monomers, it is possible to use those exemplified in [0073] to [0076].

The fluorinated copolymer of the present invention can be obtained by copolymerizing the fluorinated diene (14) or the fluorinated diene (15) with the monomer (16) in the presence of a polymerization initiating source. In a case where the fluoropolymer (16) contains monomer units derived from such other monomers, such other monomers are also subjected to copolymerization. Here, a polymerization initiating source and an organic solvent to be used at the time of copolymerization, and conditions for the copolymerization are the same as in [0079] to [0082].

The present invention provides a composition for a resist protective film characterized by comprising the above fluorinated copolymer and a solvent for dissolving the fluorinated copolymer. In the composition for a resist protective film, the solvent for dissolving the fluorinated copolymer and the proportion of the respective components are the same as in [0100] to Among the solvents exemplified in [0100], an alcohol, a ketone, a monoalkyl ether ester, a perfluoroether, a fluoroalcohol and a fluoroketone are preferred.

Further, the composition for a resist protective film of the present invention is applied on a resist film by spin coating, and the solvent is preferably a solvent which does not dissolve the resist film, and particularly preferably an alcohol, a perfluoroether, a fluoroalcohol or a fluoroketone.

The composition for a resist protective film of the present invention is preferably employed in such a manner that the respective components are uniformly mixed, followed by filtration by means of a filter having a pore diameter of from 0.1 to 2 μm.

The composition for a resist protective film of the present invention is applied on a resist film on a substrate such as a silicon wafer, followed by drying to form a resist protective film. As the coating method, spin coating, cast coating or roll coating may, for example, be employed. The formed resist protective film will be irradiated with light through a mask having a pattern drawn thereon, and then development treatment is carried out, followed by removing the resist protective film to form a pattern of the resist film.

The composition for a resist protective film of the present invention may widely be used for the purpose of protecting a resist film in a lithography process. However, such a composition is preferably used in a liquid immersion lithography process to be employed for improving the resolution. In the liquid immersion lithography process, water or other liquid immersion medium such as a solution of an organic compound containing fluorine atoms is placed in between an irradiation light source (particularly, a focus lens of a light source apparatus for irradiation) and a resist film to improve the resolution by utilizing the degree of the refractive index thereof. Accordingly, in the case of employing the liquid immersion lithography process, the resist film is likely to swell, or free components from the resist film are likely to elute into the liquid immersion medium, whereby a lens may be contaminated. Since the protective film formed from the composition for a resist protective film of the present invention is insoluble in the liquid immersion medium such as water and soluble in the developer, it is possible to solve the problem of swelling of the resist film in the liquid immersion lithography process or contamination of the lens due to free components from the resist film. The composition for a resist protective film of the present invention is most preferably used in the liquid immersion lithography process where water is used as a liquid immersion medium and ArF excimer laser is used as a light source.

The resist film to which the composition for a protective film of the present invention is to be applied, is not particularly limited, and ones used in a conventional lithography process are widely included.

The light for the irradiation in the lithography process may be ultraviolet rays such as g-line having wavelength of 436 nm or i-line having a wavelength of 365 nm, or far ultraviolet rays or vacuum ultraviolet rays, such as KrF excimer laser having a wavelength of 248 nm, ArF excimer laser having a wavelength of 193 nm or $F_2$ excimer laser having a wavelength of 157 nm. The composition for a resist protective film of the present invention is particularly useful for an application where ultraviolet rays having a wavelength of at most 250 nm, especially ultraviolet rays having a wavelength of at most 200 nm (such as ArF excimer laser or $F_2$ excimer laser) are used as the light source. Further, such a composition is more useful for the liquid immersion lithography process where ArF excimer laser or $F_2$ excimer laser is used as a light source, and is most useful for the liquid immersion lithography process where ArF excimer laser or $F_2$ excimer laser is used as a light source.

Further, the present invention provides a process for forming a resist pattern, which comprises forming a resist film on one main surface of a substrate, forming on said resist film a resist protective film by means of the above-described composition for a resist protective film, subjecting the substrate to exposure by immersion lithography, followed by alkali development.

Here, a material to be used for forming the resist film is not particularly limited, and it is possible to use one which is used in the conventional lithography process, but it is preferred to use the above resist composition of the present invention. The process for forming such a resist film on one main surface of a substrate is not particularly limited, but may be the same as mentioned above, and it is possible to exemplify a method of coating a substrate such as a silicon wafer by means of spin coating, cast coating or roll coating, followed by drying.

Further, the resist protective film is formed by using the above composition for a resist protective film of the present invention. By forming a resist protective film using the composition for a resist protective film of the present invention, it is possible to suppress elution of e.g. an acid-generating agent from the resist film into a liquid immersion medium, whereby a fine resist pattern can be formed. The process for forming such a resist protective film on the above resist film is not particularly limited, but may be the same as mentioned above, and it is possible to exemplify a method of coating the above resist film by e.g. spin coating, cast coating or roll coating, followed by drying.

Further, the method to carry out alkali development by exposing the above substrate having the above resist film and the above resist protective film formed thereon, by means of liquid immersion lithography is also the same as mentioned above. Water or other liquid immersion medium such as a solution of an organic compound containing fluorine atoms is placed in between an irradiation light source (particularly, a focus lens of a light source apparatus for irradiation) and a resist film, to improve the resolution by utilizing the degree of the refractive index thereof. As the alkaline developer to be used for alkali development, various alkali aqueous solutions may be employed, and sodium hydroxide, potassium hydroxide, ammonium hydroxide, tetramethylammonium hydroxide or triethylamine may, for example, be mentioned.

The light to be used in such liquid immersion lithography is not particularly limited, and it is possible to employ excimer laser of e.g. KrF or ArF.

EXAMPLES

Now, the present invention will be described in detail with reference to Examples, but it should be understood that the present invention is by no means restricted thereto.

Abbreviations used in the following Examples are as follows.

THF: tetrahydrofuran, PSt: polystyrene, R225: dichloropentafluoropropane (solvent), PFB: perfluoro butyryl peroxide, PFBPO: perfluoro benzoyl peroxide, IPP: diisopropyl peroxydicarbonate, BPO: benzoyl peroxide.

Preparation Example 1

Preparation of $CF_2$=$CFCF_2C(CF_3)(OH)CH$=$CH_2$

Into a 3 L glass reactor, 254 g of a crude liquid containing 68 wt % of $CF_2ClCFClCF_2C(O)CF_3$ and 1,500 ml of dehydrated THF were put and cooled to 0° C. 850 ml of a 1M THF solution of $CH_2$=$CHMgBr$, was dropwise added thereto in a nitrogen atmosphere over a period of about 1.5 hours. After completion of the dropwise addition, the mixture was stirred at 0° C. for 60 minutes and at room temperature for 16 hours. 850 ml of 1 N hydrochloric acid was dropwise added to such a solution, and the resultant was left to stand, whereby such a reaction solution was separated into two layers. An organic layer as the upper layer was recovered and concentrated by an evaporator, and then low boiling components were removed by distillation under reduced pressure to obtain 234 g of a crude liquid of $CF_2ClCFClCF_2C(CF_3)(OH)CH$=$CH_2$.

Then, into a 500 ml glass reactor which was placed in a water bath of room temperature, 47 g of zinc and 200 ml of water were put, and 234 g the above crude liquid of $CF_2ClCFClCF_2C(CF_3)(OH)CH=CH_2$ prepared was dropwise added thereto over a period of one hour. Stirring was continued after completion of the dropwise addition, and after 18 hours after completion of the dropwise addition, 20 g of zinc was further added thereto, followed by stirring for 36 hours from the initiation of the reaction. After removal by filtration of zinc remained in the reaction crude liquid, liquid separation was carried out to obtain 187 g of a crude liquid of $CF_2=CFCF_2C(CF_3)(OH)CH=CH_2$. Such a crude liquid was distilled under reduced pressure to obtain 45 g of $CF_2=CFCF_2C(CF_3)(OH)CH=CH_2$ (50° C./8.5 kPa, hereinafter referred to as "monomer 1".).

NMR spectrum of monomer 1

$^1$H-NMR (399.8 MHz, solvent: $CDCl_3$, standard: tetramethylsilane) δ (ppm): 2.98 (s, 1H), 5.72 (d, 1H), 5.88 (d, 1H), 6.02 (m, 2H).

$^{19}$F-NMR (376.2 MHz, solvent: $CDCl_3$, standard: $CFCl_3$) δ (ppm): −76.6 (m, 3F), −92.8 (m, 1F), −107.2 (m, 1F), −114.3 (m, 2F).

Example 1

Preparation of $CF_2=CFCF_2C(CF_3)(OCH_2OCH_3)CH=CH_2$

Into a 2 L glass reactor, 148 g of a crude liquid containing 68 wt % of $CF_2ClCFClCF_2C(O)CF_3$ and 860 ml of dehydrated THF were put and cooled to −20° C. 400 ml of a 1M THF solution of $CH_2=CHMgBr$ was dropwise added thereto in a nitrogen atmosphere over a period of about 1.5 hours.

After completion of the dropwise addition, the mixture was stirred at room temperature for 48 hours. Into such a reaction solution, 1,000 ml of a 2.5% NaOH aqueous solution was added for liquid separation, and an organic layer obtained was further washed with 500 g of a saturated sodium chloride aqueous solution. The organic layer was concentrated by an evaporator, and low boiling components were removed by distillation under reduced pressure to obtain 108 g of a crude liquid of $CF_2ClCFClCF_2C(CF_3)(OCH_2OCH_3)CH=CH_2$.

Then, into a 200 ml glass reactor capable of simple distillation, 27 g of zinc and 70 g of N-methyl pyrrolizinone were charged and heated to 50° C., and the pressure was reduced to 1.1 kPa. 108 g of the above prepared crude liquid of $CF_2ClCFClCF_2C(CF_3)(OCH_2OCH_3)CH=CH_2$ was dropwise added thereto over a period of one hour, and the product was continuously distilled by the simple distillation. Such a distillate was distilled under reduced pressure to obtain 25 g of $CF_2=CFCF_2C(CF_3)(OCH_2OCH_3)CH=CH_2$ (49° C./1.5 kPa, hereinafter referred to as "monomer 2").

NMR spectrum of $CF_2=CFCF_2C(CF_3)(OCH_2OCH_3)CH=CH_2$ $^1$H-NMR (399.8 MHz, solvent: $CDCl_3$, standard: tetramethylsilane) δ (ppm): 3.46 (m, 3H), 4.90 (q, 2H), 5.91 (m, 3H).

$^{19}$F-NMR (376.2 MHz, solvent: $CDCl_3$, standard: $CFCl_3$) δ (ppm): −72.6 (m, 3F), −93.3 (m, 1F), −107.3 (m, 1F), −111.3 (m, 1F), 183.5 (m, 1F).

Example 2

Preparation of $CF_2=CFCF_2C(CF_3)(OH)CH_2CH_2CH=CH_2$ 62.5 g of $CF_2=CFCF_2C(CF_3)(OH)CH_2CH_2CH=CH_2$ (47° C./1.1 kPa, hereinafter referred to as "monomer 3") was obtained by carrying out the operation in the same manner as in Preparation Example 1 except that in Preparation Example 1, a 0.5M THF solution of $CH_2=CHCH_2CH_2MgBr$ was used instead of a 1M THF solution of $CH_2=CHMgBr$.

NMR spectrum of monomer 3

$^1$H-NMR (399.8 MHz, solvent: $CDCl_3$, standard: tetramethylsilane) δ (ppm): 2.04 (t, 2H), 2.33 (q, 2H), 2.99 (br, 1H), 5.17 (dd, 2H), 5.84 (m, 1H).

$^{19}$F-NMR (376.2 MHz, solvent: $CDCl_3$, standard: $CFCl_3$) δ (ppm): −76.0 (m, 3F), −92.4 (m, 1F), −107.1 (m, 1F), −113.6 (m, 2F), −184.4 (m, 1F).

Example 3

Preparation of $CF_2=CFCF_2C(CF_3)(OCH_2OCH_3)CH_2CH_2CH=CH_2$ $CF_2=CFCF_2C(CF_3)(OCH_2OCH_3)CH_2CH_2CH=CH_2$ (hereinafter referred to as "monomer 4") can be obtained by carrying out the reatcion in the same manner as in Example 1 except that in Example 1, a 1M THF solution of $CH_2=CHCH_2CH_2MgCl$ is used instead of a 1M THF solution of $CH_2=CHMgBr$.

Example 4

Preparation of $CF_2=CFCH_2CH(C(CF_3)_2OH)CH=CH_2$

Into a 1 L glass reactor, 500 g of $CF_2ClCFClI$, 344 g of $CH_2=CHC(CF_3)_2OH$ and 32.6 g of BPO were charged and heated at 95° C. for 71 hours. A reaction crude liquid was distilled under reduced pressure to obtain 544 g of $CF_2ClCFClCH_2CHI(C(CF_3)_2OH)$ (55-58° C./0.2 kPa).

Into a 5 L glass reactor, 344 g of the above prepared $CF_2ClCFClCH_2CHI(C(CF_3)_2OH)$ and 1.7 L of a dehydrated THF were put and cooled to −70° C. 1.8 L of a 2M THF solution of $CH_2=CHMgCl$ was dropwise added thereto over a period of 4 hours.

The temperature was raised to 0° C. and stirring was carried out for 16 hours, and then 1.6 L of an aqueous saturated ammonium chloride solution was added thereto, and the temperature was raised to room temperature. It is possible to obtain $CF_2ClCFClCH_2CH(C(CF_3)_2OH)CH=CH_2$ by liquid separation of the reaction solution, concentration of the organic layer by an evaporator, followed by distillation under reduced pressure. Then, into 1 L of a glass reactor, 2 equivalent amount of zinc and 300 g of water were put and heated to 90° C. The above prepared $CF_2ClCFClCH_2CH(C(CF_3)_2OH)CH=CH_2$ was dropwise added thereto, followed by stirring for 24 hours. It is possible to obtain $CF_2=CFCH_2CH(C(CF_3)_2OH)CH=CH_2$ (hereinafter referred to as "monomer 5") by dropwise adding 70 ml of hydrochloric acid into a reaction solution and stirring for 2 hours, filtrating the reaction solution for liquid separation, followed by distillation under reduced pressure.

Example 5

Preparation of $CF_2=CFCH_2CH(C(CF_3)_2OH)CH_2CH_2CH=CH_2$ $CF_2=CFCH_2CH(C(CF_3)_2OH)CH_2CH_2CH=CH_2$ (hereinafter referred to as "monomer 6") can be obtained by carrying out the reaction in the same manner as in Example 4 except that in Example 4, a 2M THF solution of $CH_2=CHCH_2CH_2MgCl$ is used instead of 1.8 L of a 2M THF solution of $CH_2=CHMgCl$.

Example 6

Preparation of $CF_2=CFCH_2CH(C(CF_3)_2OCH_2OCH_3)CH=CH_2$ $CF_2=CFCH_2CH(C(CF_3)_2OCH_2OCH_3)CH=CH_2$ (hereinafter referred to as "monomer 7") can be obtained by carrying out the reaction in the same manner as in Example 4 except that in Example 4, $CH_2=CHC(CF_3)_2OCH_2OCH_3$ is used instead of $CH_2=CHC(CF_3)_2OH$.

Example 7

Preparation of $CF_2=CFCH_2CH(C(CF_3)_2OCH_2OCH_3)CH_2CH_2CH=CH_2$ $CF_2=CFCH_2CH(C(CF_3)_2OCH_2OCH_3)CH_2CH_2CH=CH_2$ (hereinafter referred to as "monomer 8") can be obtained by carrying out the reaction in the same manner as in Example 4 except that in Example 4, $CH_2=CHC(CF_3)_2OCH_2OCH_3$ is used instead of $CH_2=CHC(CF_3)_2OH$, and a 2M THF solution of $CH_2=CHCH_2CH_2MgCl$ is used instead of a 2M THF solution of $CH_2=CHMgCl$.

Preparation Example 2

Preparation of $CF_2=CFCH_2CH(CH_2C(CF_3)_2OH)CH=CH_2$ $CF_2=CFCH_2CH(CH_2C(CF_3)_2OH)CH=CH_2$ (hereinafter referred to as "monomer 9") can be obtained by the reaction in the same manner as in Example 4 except that in Example 4, $CH_2=CHCH_2C(CF_3)_2OH$ is used instead of $CH_2=CHC(CF_3)_2OH$.

Example 8

Preparation of $CF_2=CFCH_2CH(CH_2C(CF_3)_2OH)CH_2CH_2CH=CH_2$ $CF_2=CFCH_2CH(CH_2C(CF_3)_2OH)CH_2CH_2CH=CH_2$ (hereinafter referred to as "monomer 10") can be obtained by carrying out the reaction in the same manner as in Example 4 except that in Example 4, $CH_2=CHCH_2C(CF_3)_2OH$ is used instead of $CH_2=CHC(CF_3)_2OH$, and a 2M THF solution of $CH_2=CHCH_2CH_2MgCl$ is used instead of a 2M THF solution of $CH_2=CHMgCl$.

Example 9

Preparation of $CF_2=CFCH_2CH(CH_2C(CF_3)_2OCH_2OCH_3)CH=CH_2$ $CF_2=CFCH_2CH(CH_2C(CF_3)_2OCH_2OCH_3)CH=CH_2$ (hereinafter referred to as "monomer 11") can be obtained by carrying out the reaction in the same manner as in Example 4 except that $CH_2=CHCH_2C(CF_3)_2OCH_2OCH_3$ is used instead of $CH_2=CHC(CF_3)_2OH$.

Example 10

Preparation of $CF_2=CFCH_2CH(CH_2C(CF_3)_2OCH_2OCH_3)CH_2CH_2CH=CH_2$ $CF_2=CFCH_2CH(CH_2C(CF_3)_2OCH_2OCH_3)CH_2CH_2CH=CH_2$ (hereinafter referred to as "monomer 12") can be obtained by carrying out the reaction in the same manner as in Example 4 except that in Example 4, $CH_2=CHCH_2C(CF_3)_2OCH_2OCH_3$ is used instead of $CH_2=CHC(CF_3)_2OH$, and a 2M THF solution of $CH_2=CHCH_2CH_2MgCl$ is used instead of 2M THF solution of $CH_2=CHMgCl$.

Preparation Example 3

4.50 g of monomer 1 and 4.77 g of ethyl acetate were charged into a pressure resistant reactor made of glass and having an internal capacity of 30 mL. Then, 9.02 g of R225 solution containing 3 wt % of PFB as a polymerization initiator (hereinafter referred to as PFB/R225 solution) was added thereto. The interior of the system was freeze-deaerated, and then the reactor was sealed, followed by polymerization for 18 hours in a constant temperature shaking bath (20° C.). After the polymerization, the reaction solution was dropped into hexane to reprecipitate the polymer, followed by vacuum drying at 80° C. for 20 hours. As a result, 3.95 g of a non-crystalline polymer having a fluorinated cyclic structure in its main chain (hereinafter referred to as "polymer 1A-1"), was obtained. The molecular weight measured by GPC (gel permeation chromatography) employing THF as a solvent and calculated as PSt, was such that the number average molecular weight (Mn) was 8,300, and the weight average molecular weight (Mw) was 18,200, and Mw/Mn=2.19. Tg measured by the differential scanning calorimetry (DSC) was 86° C., and the polymer was a white powder at room temperature.

The polymer obtained was soluble in acetone, THF, ethyl acetate, methanol and 2-perfluorohexylmethanol, and was insoluble in R225, perfluoro(2-butyltetrahydrofuran) and perfluoro-n-octane.

By $^{19}$F-NMR and $^1$H-NMR, it was confirmed to be a cyclized polymer having the following monomer units of (1a) and (1b).

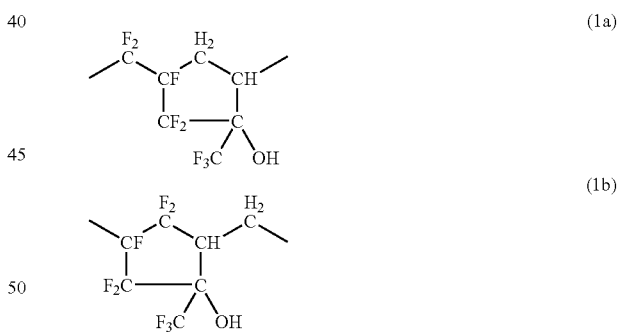

Preparation Example 4

5.00 g of monomer 1 and 7.50 g of ethyl acetate were charged into a pressure resistant reactor made of glass and having an internal capacity of 30 mL. Then, 0.1875 g of PFBPO was added as a polymerization initiator. The interior of the system was freeze-deaerated, and then the reactor was sealed, followed by polymerization for 18 hours in a constant temperature shaking bath (70° C.). After the polymerization, the reaction solution was dropped into hexane to reprecipitate the polymer, followed by vacuum drying at 80° C. for 24 hours. As a result, 2.86 g of a non-crystalline polymer having a fluorinated cyclic structure in its main chain (hereinafter referred to as "polymer 1A-2") was obtained. The molecular weight measured by GPC employing THF as a solvent and calculated as PSt was such that the number average molecular weight (Mn) was 5,700, and the weight average molecular weight (Mw) was 12,800, and Mw/Mn=2.25. Tg measured by the differential scanning calorimetry (DSC) was 83° C., and the polymer was a white powder at room temperature.

The polymer obtained was soluble in acetone, THF, ethyl acetate, methanol and 2-perfluorohexylethanol, and was insoluble in R225, perfluoro(2-butyltetrahydrofuran) and perfluoro-n-octane.

Example 11

2.50 g of monomer 1, 1.64 g of monomer 2 and 1.11 g of ethyl acetate were charged into a pressure resistant reactor made of glass and having an internal capacity of 20 mL. Then, 5.11 g of PFB/R225 solution was added as a polymerization initiator. The interior of the system was freeze-deaerated, and then the reactor was sealed, followed by polymerization for 18 hours in a constant temperature shaking bath (20° C.). After the polymerization, the reaction solution was dropped into hexane to reprecipitate the polymer, followed by vacuum drying at 60° C. for 24 hours. As a result, 2.89 g of a non-crystalline polymer having a fluorinated cyclic structure in its main chain (hereinafter referred to as "polymer 2A"), was obtained. The molecular weight measured by GPC employing THF as a solvent and calculated as PSt was such that the number average molecular weight (Mn) was 10,000, and the weight average molecular weight (Mw) was 19,800, and Mw/Mn=1.99.

Tg measured by differential scanning calorimetry (DSC) was 91.8° C., and the polymer was a white powder at room temperature. The polymer composition calculated by $^{19}$F-NMR and $^1$H-NMR was such that repeating units made of monomer 1/repeating units made of monomer 2=84/16 mol %.

The polymer obtained was soluble in acetone, THF, ethyl acetate and methanol, and was insoluble in R225, perfluoro(2-butyltetrahydrofuran) and pefluoro-n-octane.

Example 12

4.00 g of monomer 3 and 16.0 g of ethyl acetate were charged into a pressure resistant reactor made of glass and having an internal capacity of 30 mL. Then, 0.300 g of IPP was added as a polymerization initiator. The interior of the system was freeze-deaerated, and then the reactor was sealed, followed by polymerization for 18 hours in a constant temperature shaking bath (40° C.). After the polymerization, the reaction solution was dropped into hexane to reprecipitate the polymer, followed by vacuum drying at 100° C. for 24 hours. As a result, 3.94 g of a non-crystalline polymer having a fluorinated cyclic structure in its main chain (hereinafter referred to as "polymer 1B"), was obtained. The molecular weight measured by GPC employing THF as a solvent and calculated as PSt, was such that the number average molecular weight (Mn) was 7,600, and the weight average molecular weight (Mw) was 17,700, and Mw/Mn=2.33. Tg measured by the differential scanning calorimetry (DSC) was 169° C., and the polymer was a white powder at room temperature.

The polymer obtained was soluble in acetone, THF, ethyl acetate, methanol, 2-perfluorohexylethanol, and was insoluble in R225, perfluoro(2-butyltetrahydrofuran) and pefluoro-n-octane.

By 19F-NMR and $^1$H-NMR, it was confirmed to be a cyclized polymer having the following monomer units of (1c).

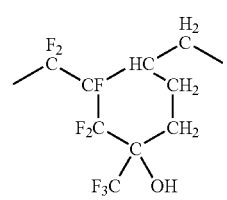

(1c)

Example 13

A non-crystalline polymer having a fluorinated cyclic structure in its main chain (hereinafter referred to as "polymer 2B") can be obtained by carrying out the reaction in the same manner as in Example 11 except that in Example 11, monomer 3 obtained in Example 2 is used instead of monomer 1, and monomer 4 obtained in Example 3 is used instead of monomer 2.

Example 14

A non-crystalline polymer having a fluorinated cyclic structure in its main chain (hereinafter referred to as "polymer 1C") was obtained by carrying out the reaction in the same manner as in Preparation Example 3 except that in Preparation Example 3, monomer 5 obtained in Example 4 was used instead of monomer 1. The polymer was a white powder at room temperature, and the polymer obtained was soluble in acetone, THF and methanol, and was insoluble in R225, perfluoro(2-butyltetrahydrofuran) and perfluoro-n-octane.

By $^{19}$F-NMR and $^1$H-NMR, it was confirmed to be a cyclized polymer having the following monomer units of (1d) and (1e).

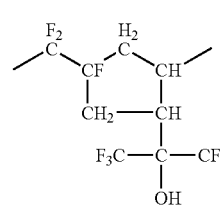

(1d)

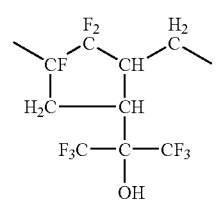

(1e)

Example 15

A non-crystalline polymer having a fluorinated cyclic structure in its main chain (hereinafter referred to as "polymer 1D") was obtained by carrying out the reaction in the same manner as in Preparation Example 3 except that in Preparation Example 3, monomer 6 obtained in Example 5 was used instead of monomer 1. The polymer was a white powder at room temperature, and such a polymer was soluble in acetone, THF and methanol and was insoluble in R225, perfluoro(2-butyltetrahydrofuran) and perfluoro-n-octane.

By $^{19}$F-NMR and $^1$H-NMR, it was confirmed to be a cyclized polymer having the following monomer units of (1f).

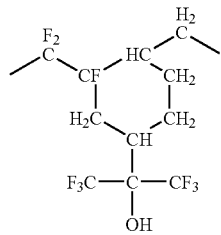
(1f)

Example 16

A non-crystalline polymer having a fluorinated cyclic structure in its main chain (hereinafter referred to as "polymer 2C") can be obtained by carrying out the reaction in the same manner as in Example 11 except that in Example 11, monomer 5 obtained in Example 4 is used instead of monomer 1, and monomer 7 obtained in Example 6 is used instead of monomer 2.

Example 17

A non-crystalline polymer having a fluorinated cyclic structure in its main chain (hereinafter referred is to as "polymer 2D") can be obtained by carrying out the reaction in the same manner as in Example 11 except that monomer 6 obtained in Example 5 is used instead of monomer 1, and monomer 8 obtained in Example 7 is used instead of monomer 2.

Preparation Example 5

A non-crystalline polymer having a fluorinated cyclic structure in its main chain (hereinafter referred to as "polymer 1E") was obtained by carrying out the reaction in the same manner as in Preparation Example 3 except that in Preparation Example 3, monomer 9 obtained in Preparation Example 2 was used instead of monomer 1. The polymer was a white powder at room temperature, and such a polymer was soluble in acetone, THF and methanol, and was insoluble in R225, perfluoro(2-butyltetrahydrofuran) and perfluoro-n-octane.

By $^{19}$F-NMR and $^1$H-NMR, it was confirmed to be a cyclized polymer having the following monomer units of (2d) and (2e).

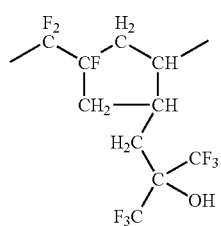
(2d)

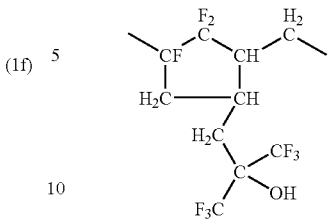
(2e)

Example 18

A non-crystalline polymer having a fluorinated cyclic structure in its main chain (hereinafter referred to as "polymer 1F") was obtained by carrying out the reaction in the same manner as in Preparation Example 3 except that in Preparation Example 3, monomer 10 obtained in Example 8 was used instead of monomer 1. The polymer was a white powder at room temperature, and such a polymer was soluble in acetone, THF and methanol, and was insoluble in R225, perfluoro(2-butyltetrahydrofuran) and perfluoro-n-octane.

By $^{19}$F-NMR and $^1$H-NMR, it was confirmed to be a cyclized polymer having the following monomer units of (2f).

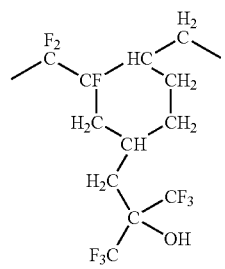
(2f)

Example 19

A non-crystalline polymer having a fluorinated cyclic structure in its main chain (hereinafter referred to as "polymer 2E") can be obtained by carrying out the reaction in the same manner as in Example 11 except that in Example 11, monomer 9 obtained in Preparation Example 2 is used instead of monomer 1, and monomer 11 obtained in Example 9 is used instead of monomer 2.

Example 20

A non-crystalline polymer having a fluorinated cyclic structure in its main chain (hereinafter referred to as "polymer 2F") can be obtained by carrying out the reaction in the same manner as in Example 11 except that in Example 11, monomer 10 obtained in Example 8 is used instead of monomer 1, and monomer 12 obtained in Example 10 is used instead of monomer 2.

Example 21

By employing polymer 1A-1 obtained in Preparation Example 3, a methanol solution of sodium hydroxide and (1-adamantylmethyl)chloromethyl ether, it is possible to obtain a polymer having some hydroxyl groups of polymer 1A-1 converted to adamantylmethoxymethyl (hereinafter referred to as "polymer 3A").

Example 22

By employing polymer 2A obtained in Example 11, a methanol solution of sodium hydroxide, and (1-adamantylmethyl)chloromethyl ether, it is possible to obtain a polymer having some hydroxyl groups of polymer 2A converted to adamantylmethoxymethyl (hereinafter referred to as "polymer 3B").

Example 23

By employing polymer 1C obtained in Example 14, a methanol solution of sodium hydroxide, and (1-adamantylmethyl)chloromethyl ether, it is possible to obtain a polymer having some hydroxyl groups of polymer 1C converted to adamantylmethoxymethyl (hereinafter referred to as "polymer 3C").

Example 24

By employing polymer 1D obtained in Example 15, a methanol solution of sodium hydroxide, and (1-adamantylmethyl)chloromethyl ether, it is possible to obtain a polymer having some hydroxyl groups of polymer 1D converted to adamantylmethoxymethyl (hereinafter referred to as "polymer 3D").

Example 25

By employing polymer 1E obtained in Preparation Example 5, a methanol solution of sodium hydroxide, and (1-adamantylmethyl)chloromethyl ether, it is possible to obtain a polymer having some hydroxyl groups of polymer 1E converted to adamantylmethoxymethyl (hereinafter referred to as "polymer 3E").

Example 26

By employing polymer 1F obtained in Example 18, a methanol solution of sodium hydroxide, and (1-adamantylmethyl)chloromethyl ether, it is possible to obtain a polymer having some hydroxyl groups of polymer 1F converted to adamantylmethoxymethyl (hereinafter referred to as "polymer 3F").

Example 27

4.48 g of monomer 2, 2.30 g of 1,1,2,3,3-pentafluoro-4-hydroxy-4-trifluoromethyl-1,6-heptadiene (hereinafter referred to as "monomer 13"), 0.36 g of 1,4-dioxane and 14.34 g of ethyl acetate were charged into a pressure resistant rector made of glass and having an internal capacity of 30 mL. Then, 18.20 g of a PFB/R225 solution was added as a polymerization initiator. The interior of the system was freeze-deaerated, and then the reactor was sealed, followed by polymerization for 18 hours in a constant temperature shaking bath (20° C.). After the polymerization, the reaction solution was dropped into hexane to reprecipitate the polymer, followed by vacuum drying at 100° C. for 18 hours. As a result, 2.72 g of a non-crystalline polymer having a fluorinated cyclic structure in its main chain (hereinafter referred to as "polymer 1G") was obtained.

Tg measured by the differential scanning calorimetry (DSC) was 133° C., and the polymer was a white powder at room temperature. The polymer composition calculated by $^{19}$F-NMR and $^1$H-NMR was such that repeating units made of monomer 2/repeating units made of 1,1,2,3,3-pentafluoro-4-hydroxy-4-trifluoromethyl-1,6-heptadiene=89/11

The polymer obtained was soluble in acetone, THF, ethyl acetate, methanol and 2-perfluorohexylethanol, and was insoluble in perfluoro(2-butyltetrahydrofuran) and perfluoro-n-octane.

Preparation Example 6

4.30 g of monomer 13, 0.40 g of monomer 1 and 9.11 g of ethyl acetate were charged into a pressure resistant rector made of glass and having an internal capacity of 20 mL. Then, 0.208 g IPP was added as a polymerization initiator. The interior of the system was freeze-deaerated, and then the reactor was sealed, followed by polymerization for 18 hours in a constant temperature shaking bath (40° C.). After the polymerization, the reaction solution was dropped into hexane to reprecipitate the polymer, followed by vacuum drying at 100° C. for 24 hours. As a result, 3.78 g of a non-crystalline polymer having a fluorinated cyclic structure in its main chain (hereinafter referred to as "polymer 1H") was obtained. The molecular weight measured by GPC employing THF and R225 as a solvent and calculated as PSt was such that the number average molecular weight (Mn) was 2,800, and the weight average molecular weight (Mw) was 57,100, and Mw/Mn=2.74.

Tg measured by the differential scanning calorimetry (DSC) was 153° C., and the polymer was a white powder at room temperature. The polymer composition calculated by $^{19}$F-NMR and $^1$H-NMR was such that repeating units made of monomer 13/repeating units made of monomer 1=92/8 mol %.

The polymer obtained was soluble in acetone, THF, ethyl acetate and methanol, and was insoluble in R225, perfluoro (2-butyltetrahydrofuran) and perfluoro-n-octane.

Example 28

2.24 g of polymer 1H obtained in the same manner as in Preparation Example 6 and 47 g of methanol were charged into a glass flask having an internal capacity of 200 ml. Into such a solution, 4.18 g of methanol containing 2.0 wt % of sodium hydroxide was added, followed by stirring at room temperature for 12 hours. Such a reaction solution was concentrated by an evaporator, followed by vacuum drying to remove methanol. To a polymer powder obtained, 60 g of THF was added, and then 0.35 g of chloromethyl methyl ether was added thereto, followed by stirring at room temperature. After 12 hours from the initiation of stirring, the reaction solution became whitely turbid, and such a reaction solution was concentrated by an evaporator, followed by vacuum drying to remove THF. To a polymer powder obtained, 20 g of ethyl acetate was added, followed by washing with 100 g of water to recover an ethyl acetate layer. Such an ethyl acetate layer was dropwise added to highly excessive hexane to reprecipitate the polymer, followed by vacuum drying at 100° C. for 24 hours. As a result, 2.11 g of a non-crystalline polymer having fluorinated cyclic structures in its main chain (hereinafter referred to as "polymer 1I") was obtained. The molecular weight measured by GPC employing THF and R225 as solvents, and calculated as PSt, was such that the number average molecular weight (Mn) 22,700, and the weight average molecular weight (Mw) was 57,600, and Mw/Mn=2.54.

Tg measured by the differential scanning calorimetry (DSC) was 151° C., and the polymer was a white powder at room temperature. By $^{19}$F-NMR and $^{1}$H-NMR, 20.5% of hydroxyl groups in such a polymer were found to be converted to methoxymethyl ether.

The polymer obtained was soluble in acetone, THF, ethyl acetate and methanol, and was insoluble in R225, perfluoro (2-butyltetrahydrofuran) and perfluoro-n-octane.

Example 29

4.00 g of monomer 13, 0.71 g of CF$_2$=CFCF$_2$C(CF$_3$)(OCH$_2$OCH$_3$)CH$_2$CH=CH$_2$ (hereinafter referred to as "monomer 14"), 0.62 g of monomer 2 and 13.83 g of ethyl acetate were charged into a pressure resistant reactor made of glass and having an internal capacity of 30 mL. Then, 0.287 g of IPP was added as a polymerization initiator. The interior of the system was freeze-deaerated, and then the reactor was sealed, followed by polymerization for 18 hours in a constant temperature shaking bath (40° C.). After the polymerization, the reaction solution was dropped into hexane to reprecipitate the polymer, followed by vacuum drying at 100° C. for 24 hours. As a result, 4.16 g of a non-crystalline polymer having a fluorinated cyclic structure in its main chain (hereinafter referred to as "polymer 1J") was obtained. The molecular weight measured by GPC employing THF and R225 as solvents and calculated as PSt, was such that the number average molecular weight (Mn) was 17,700, and the weight average molecular weight (Mw) was 46,300, and Mw/Mn=2.63.

Tg measured by the differential scanning calorimetry (DSC) was 145° C., and the polymer was a white powder at room temperature. The polymer composition calculated by $^{19}$F-NMR and $^{1}$H-NMR was such that repeating units made of monomer 13/repeating units made of monomer 14/repeating units made of monomer 2=79/14/7 mol %.

The polymer obtained was soluble in acetone, THF, ethyl acetate and methanol, and was insoluble in R225, perfluoro (2-butyltetrahydrofuran) and perfluoro-n-octane.

Example 30

1.30 g of monomer 1, 0.96 g of monomer 3 and 3.39 g of ethyl acetate were charged into a pressure resistant reactor made of glass and having an internal capacity of 30 mL. Then, 5.67 g of a PFB/R225 solution was added as a polymerization initiator. The interior of the system was freeze-deaerated, and then the reactor was sealed, followed by polymerization for 18 hours in a constant temperature shaking bath (20° C.). After the polymerization, the reaction solution was dropped into hexane to reprecipitate the polymer, followed by vacuum drying at 100° C. for 24 hours. As a result, 1.77 g of a non-crystalline polymer having a fluorinated cyclic structure in its main chain (hereinafter referred to as "polymer 1K") was obtained. The molecular weight measured by GPC employing THF and R225 as solvents and calculated as PSt, was such that the number average molecular weight (Mn) was 14,300, and the weight average molecular weight (Mw) was 23,800, and Mw/Mn=1.67.

Tg measured by differential scanning calorimetry (DSC) was 126° C., and the polymer was a white powder at room temperature. The polymer composition calculated by $^{19}$F-NMR and $^{1}$H-NMR was such that repeating units made of monomer 1/repeating units made of monomer 3=51/49 mol %.

The polymer obtained was soluble in acetone, THF, ethyl acetate and methanol, and was insoluble in R225, perfluoro (2-butyltetrahydrofuran) and perfluoro-n-octane.

Example 31

0.55 g of monomer 1, 0.68 g of monomer 2, 0.81 g of monomer 3 and 2.98 g of ethyl acetate were charged into a pressure resistant reactor made of glass and having an internal capacity of 30 mL. Then, 5.03 g of a PFB/R225 solution was added as a polymerization initiator. The interior of the system was freeze-deaerated, and then the reactor was sealed, followed by polymerization for 18 hours in a constant temperature shaking bath (20° C.). After the polymerization, the reaction solution was dropped into hexane to reprecipitate the polymer, followed by vacuum drying at 80° C. for 24 hours. As a result, 1.20 g of a non-crystalline polymer having a fluorinated cyclic structure in its main chain (hereinafter referred to as "polymer 1L") was obtained. The molecular weight measured by GPC employing THF and R225 as solvents and calculated as PSt, was such that the number average molecular weight (Mn) was 12,800, and the weight average molecular weight (Mw) was 22,100, and Mw/Mn=1.72.

Tg measured by the differential scanning calorimetry (DSC) was 118° C., and the polymer was a white powder at room temperature. The polymer composition calculated by $^{19}$F-NMR and $^{1}$H-NMR was such that repeating units made of monomer 1/repeating units made of monomer 2/repeating units made of monomer 3=22/18/60 mol %.

The polymer obtained was soluble in acetone, THF, ethyl acetate and methanol, and was insoluble in R225, perfluoro (2-butyltetrahydrofuran) and perfluoro-n-octane.

Preparation Example 7

11.5 g of 1,1,2,3,3-pentafluoro-4-trifluoromethyl-4-hydroxy-1,6-heptadiene[CF$_2$=CFCF$_2$C(CF$_3$)(OH)CH$_2$CH=CH$_2$] and 10.6 g of ethyl acetate were charged into a pressure resistant reactor made of glass and having an internal capacity of 50 cc. Then, 0.23 g of IPPO was added as a polymerization initiator. The interior of the system was freeze-deaerated, followed by polymerization for 18 hours in a constant temperature shaking bath (40° C.). After the polymerization, the reaction solution was dropped into hexane to reprecipitate the polymer, followed by vacuum drying at 140° C. for 20 hours. As a result, 8 g of a non-crystalline polymer having a fluorinated cyclic structure in its main chain (hereinafter referred to as "polymer 1M") was obtained. The molecular weight measured by GPC employing THF as a solvent and calculated as PSt, was such that the number average molecular weight (Mn) was 6,500, and the weight average molecular weight (Mw) was 22,000, and Mw/Mn=3.38. Tg measured by the differential scanning calorimetry (DSC) was 152° C., and the polymer was a white powder at room temperature. The polymer obtained was soluble in acetone, THF, ethyl acetate, methanol and R225, and was insoluble in hexane.

Preparation Example 8

11.0 g of fluorinated diene[CF$_2$=CFCH$_2$CH(C(CF$_3$)$_2$OH)CH$_2$CH=CH$_2$], 0.92 g of ethyl acetate and 14.4 g of AK225 (dichloropentafluoropropane) were charged into a pressure resistant reactor made of glass and having an internal capacity of 50 mL. Then, 0.52 g of PFB was added as a polymerization initiator. The interior of the system was freeze-deaerated, and then the reactor was sealed, followed by polymerization for 18 hours in a constant temperature shaking bath (20° C.). After the polymerization, the reaction solution was diluted with R225 and dropwise added into hexane to reprecipitate the polymer, followed by vacuum drying at 100° C. for 18 hours. As a result, 10.6 g of a non-crystalline polymer having a fluorinated cyclic structure in its main chain (hereinafter referred to as "polymer 1N") was obtained. The molecular weight measured by GPC employing THF as a solvent and calculated as PSt, was such that the number average molecular weight (Mn) was 14,800, and the weigh average molecular weight (Mw) was 25,600, and Mw/Mn=1.72. Tg measured by differential scanning calorimetry (DSC) was 118° C., and the polymer was a white powder at room temperature. The polymer obtained was soluble in acetone, THF, ethyl acetate, methanol and R225 and was insoluble in hexane.

Examples 32 to 35

1 g of each of polymers 1A-1, 2A, 1M and 1N prepared in Preparation Example 3, Example 11, Preparation Example 7 and Preparation Example 8 was dissolved in 10 g of 2-heptanone, and filtrated through a filter made of PTFE (polytetrafluoroethylene) having a pore diameter of 0.2 μm to obtain a composition for a resist protective film.

The above composition for a resist protective film was spin-coated on a silicon substrate, followed by heat treatment at 100° C. for 90 seconds to form a resist protective film having a thickness of 0.20 μm. The light transmittance of the resist protective film thus obtained is shown in Table 1.

TABLE 1

| | Polymer | Transmittance of light of 193 nm (%) | Transmittance of light of 157 nm (%) |
|---|---|---|---|
| Ex. 32 | 1A-1 | 99.3 | 79.4 |
| Ex. 33 | 2A | 97.6 | 65.1 |
| Ex. 34 | 1M | 99.1 | 79.0 |
| Ex. 35 | 1N | 99.6 | 90.2 |

Examples 36 and 37

0.7 g of each of polymers 2A and 1G prepared in Example 11 and Example 27, and 0.035 g of triphenylsulfonium triflate were dissolved in 10 g of 2-heptanone, and filtrated through a filter made of PTFE and having a pore diameter of 0.2 μm to obtain a resist composition.

The above resist composition was spin-coated on a silicon substrate, followed by heat treatment at 100° C. for 90 seconds to form a resist film having a thickness of 0.20 μm. The light transmittance of the resist film thus obtained is shown in Table 2.

TABLE 2

| | Polymer | Transmittance of light of 193 nm (%) | Transmittance of light of 157 nm (%) |
|---|---|---|---|
| Ex. 36 | 2A | 65.0 | 57.1 |
| Ex. 37 | 1G | 63.0 | 55.0 |

Examples 38 to 40

0.3 g of each of polymers 1A-1, 1M and 1N prepared in Preparation Example 3, Preparation Example 7 and Preparation Example 8 was dissolved in 10 g of 2-heptanone and filtrated through a filter made of PTFE and having a pore diameter of 0.2 μm to obtain a composition for a resist protective film.

Then, the above composition for a resist protective film was spin-coated on a silicon substrate treated with hexamethyldisilazane, followed by heat treatment at 100° C. for 90 seconds to form a resist protective film having a thickness of 0.15 μm. The contact angle to water of the resist protective film thus obtained was measured. The results are shown in Table 3.

TABLE 3

| | Polymer | Contact angle (°) |
|---|---|---|
| Ex. 38 | 1A-1 | 81 |
| Ex. 39 | 1M | 70 |
| Ex. 40 | 1N | 74 |

Examples 41 to 43

The resist protective films on the silicon substrates prepared in Examples 38 to 40 were immersed in water and alkali developer for 30 seconds, followed by drying at 110° C. for 90 seconds to measure a change in film thickness before and after immersion in water and alkali developer. The results are shown in Table 4.

TABLE 4

| | Polymer | Change in film thickness after immersion into water | Change in film thickness after immersion into developer |
|---|---|---|---|
| Ex. 41 | 1A-1 | Not changed | Changed |
| Ex. 42 | 1M | Not changed | Changed |
| Ex. 43 | 1N | Not changed | Changed |

Examples 46 to 48

1 g of each of polymers 1A-1, 1M and 1N prepared in Preparation Examples 3, 7 and 8 was dissolved in 10 g of 2-heptanone, and filtrated through a filter made of PTFE and having a pore diameter of 0.2 μm to obtain a composition for a resist protective film.

The above composition for a resist protective film was spin-coated on a silicon substrate, followed by heat treatment at 100° C. for 90 seconds to form a resist protective film having a thickness of 0.20 μm. The refractive index to the light beams of 193 nm of the resist protective film thus obtained was measured by spectroscopic ellipsometer (M2000D) manufactured by J. A. Woollam Co., Inc. The results are shown in Table 5.

TABLE 5

| | Polymer | Transmittance of light of 193 nm (%) |
|---|---|---|
| Ex. 46 | 1A-1 | 1.46 |
| Ex. 47 | 1M | 1.48 |
| Ex. 48 | 1N | 1.49 |

Preparation Example 9

Preparation of 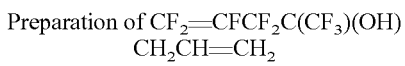

Into a 2 L reactor made of glass, 108 g of $CF_2ClCFClCF_2C(O)CF_3$ and 500 ml of dehydrated THF were charged and cooled to 0° C. A diluted solution having 200 ml of a 2M THF solution of $CH_2$=$CHCH_2MgCl$ further diluted with 200 ml of dehydrated THF, was dropwise added thereto in a nitrogen atmosphere over a period of about 5.5 hours. After completion of the dropwise addition, the mixture was stirred at 0° C. for 30 minutes and at room temperature for 17 hours, whereupon 200 ml of 2N hydrochloric acid was dropwise added. 200 ml of water and 300 ml of diethyl ether were added for liquid separation, and a diethyl ether layer was obtained as an organic layer. The organic layer was dried over magnesium sulfate, followed by filtration to obtain a crude liquid. The crude liquid was concentrated by an evaporator, followed by distillation under reduced pressure to obtain 85 g of $CF_2ClCFClCF_2C(CF_3)(OH)CH_2CH$=$CH_2$ (60 to 66° C./0.7 kPa).

Then, into a 500 ml reactor made of glass, 81 g of zinc and 170 ml of dioxane were put, and activation of zinc was carried out by iodine. The reactor was heated to 100° C., and a solution prepared by diluting 84 g of $CF_2ClCFClCF_2C(CF_3)(OH)CH_2CH$=$CH_2$ prepared as described above, with 50 ml of dioxane, was dropwise added thereto over a period of 1.5 hours. After completion of the dropwise addition, the mixture was stirred at 100° C. for 40 hours. The reaction solution was filtrated and washed with a small amount of dioxane. The filtrate was distilled under reduced pressure to obtain 30 g of $CF_2$=$CFCF_2C(CF_3)(OH)CH_2CH$=$CH_2$ (36 to 37° C./1 kPa, hereinafter referred to as "monomer 15").

Preparation Example 10

Preparation of $CF_2$=$CFCH_2CH(C(CF_3)_2OH)CH_2CH$=$CH_2$

Into a 1 L glass reactor, 500 g of $CF_2ClCFClI$, 344 g of $CH_2$=$CHC(CF_3)_2OH$ and 32.6 g of BPO were charged and heated to 95° C. for 71 hours. The reaction crude liquid was distilled under reduced pressure to obtain 544 g of $CF_2ClCFClCH_2CHI(C(CF_3)_2OH)$ (55 to 58° C./0.2 kPa).

Into a 5 L glass reactor, 344 g of the above prepared $CF_2ClCFClCH_2CHI(C(CF_3)_2OH)$ and 1.7 L of dehydrated THF were put and cooled to −70° C. 1.8 L of a 2M THF solution of $CH_2$=$CHCH_2MgCl$ was dropwise added thereto over a period of 4 hours.

The temperature was raised to 0° C. and stirring was carried out for 16 hours, and then 1.6 L of an aqueous saturated ammonium chloride solution was added thereto, and the temperature was raised to room temperature. The reaction solution was subjected to liquid separation, and the organic layer was concentrated by an evaporator and then distilled under reduced pressure to obtain 287 g of $CF_2ClCFClCH_2CH(C(CF_3)_2OH)CH_2CH$=$CH_2$ (62-66° C./0.2 kPa). Into a 1 L glass reactor, 97 g of zinc and 300 g of water were put and heated to 90° C. Then, 287 g of the above prepared $CF_2ClCFClCH_2CH(C(CF_3)_2OH)CH_2CH$=$CH_2$ was dropwise added thereto, followed by stirring for 24 hours. 70 mL of hydrochloric acid was dropwise added to the reaction solution, followed by stirring for 2 hours. The reaction solution was filtrated and subjected to liquid separation and then distilled under reduced pressure to obtain 115 g of $CF_2$=$CFCH_2CH(C(CF_3)_2OH)CH_2CH$=$CH_2$ (53-54° C./1 kPa, hereinafter referred to as "monomer 16").

Example 49

5.0 g of monomer 15 obtained in Preparation Example 9, 0.35 g of vinyl acetate and 18.2 g of ethyl acetate were charged into a pressure resistant reactor made of glass and having an internal capacity of 30 mL. Then, 0.35 g of IPP was added as a polymerization initiator. The interior of the system was vacuum-deaerated, followed by polymerization for 18 hours in a constant temperature shaking bath (40° C.). After the polymerization, the reaction solution was dropped into hexane to reprecipitate the polymer, followed by vacuum drying at 110° C. for 24 hours. As a result, 4.51 g of a non-crystalline polymer having a fluorinated cyclic structure in its main chain (hereinafter referred to as "polymer 5A") was obtained. The molecular weight measured by GPC employing THF as a solvent and calculated as PSt, was such that the number average molecular weight (Mn) was 5,800, and the weight average molecular weight (Mw) was 12,800, and Mw/Mn=2.19.

Tg measured by the differential scanning calorimetry (DSC) was not detected. The polymer was a white powder is at room temperature.

The polymer obtained was soluble in acetone, THF, ethyl acetate and methanol, and was insoluble in R225, perfluoro (2-butyltetrahydrofuran) and perfluoro-n-octane.

Example 50

3.0 g of monomer 1 obtained in Preparation Example 1, 0.43 g of vinyl acetate and 13.7 g of ethyl acetate were charged into a pressure resistant reactor made of glass and having an internal capacity of 30 mL. Then, 0.257 g of IPP was added as a polymerization initiator. The interior of the system was freeze-deaerated, followed by polymerization for 18 hours in a constant temperature shaking bath (40° C.). After the polymerization, the reaction solution was dropped into hexane to reprecipitate the polymer, followed by vacuum drying at 90° C. for 24 hours. As a result, 3.16 g of a non-crystalline polymer having a fluorinated cyclic structure in its main chain (hereinafter referred to as "polymer 6A") was obtained. The molecular weight measured by GPC employing THF as a solvent and calculated as PSt, was such that the number average molecular weight (Mn) was 13,000, and the weight average molecular weight (Mw) was 17,500, and Mw/Mn=1.35.

The polymer was a white powder at room temperature. The polymer obtained was soluble in acetone, THF, ethyl acetate, methanol and R225, and was insoluble in a is fluoro(2-butyltetrahydrofuran) and perfluoro-n-octane.

Example 51

3.0 g of monomer 1 obtained in Preparation Example 1, 1.01 g of vinyl acetate and 16.0 g of ethyl acetate were charged into a pressure resistant reactor made of glass and having an internal capacity of 30 mL. Then, 0.301 g of IPP was added as a polymerization initiator. The interior of the system was freeze-deaerated, followed by polymerization for 18 hours in a constant temperature shaking bath (40° C.). After the polymerization, the reaction solution was dropped into hexane to reprecipitate the polymer, followed by vacuum drying at 80° C. for 24 hours. As a result, 2.69 g of a non-crystalline polymer having a fluorinated cyclic structure in its main chain (hereinafter referred to as "polymer 6B") was obtained. The molecular weight measured by GPC employing THF as a solvent and calculated as PSt, was such that the number average molecular weight (Mn) was 6,400, the weight average molecular weight (Mw) was 13,200, and Mw/Mn=2.05.

Tg measured by differential scanning calorimetry (DSC) was 86° C., and the polymer was a white powder at room temperature.

Example 52

2.0 g of monomer 1 obtained in Preparation Example 1, 0.78 g of vinyl propionate and 11.1 g of ethyl acetate were charged into a pressure resistant reactor made of glass and having an internal capacity of 30 mL. Then, 0.209 g of IPP was added as a polymerization initiator. The interior of the system was freeze-deaerated, followed by polymerization for 18 hours in a constant temperature shaking bath (40° C.). After the polymerization, the reaction solution was dropped into hexane to reprecipitate the polymer, followed by vacuum drying at 80° C. for 24 hours. As a result, 2.55 g of a non-crystalline polymer having a fluorinated cyclic structure in its main chain (hereinafter referred to as "polymer 6C") was obtained. The molecular weight measured by GPC employing THF as a solvent and calculated as PSt, was such that the number average molecular weight (Mn) was 7,300, the weight average molecular weight (Mw) was 13,700, and Mw/Mn=1.88.

Tg measured by differential scanning calorimetry (DSC) was 82° C., and the polymer was a white powder at room temperature. The polymer composition calculated by $^{19}$F-NMR and $^1$H-NMR was such that repeating units made of monomer 1/repeating units made of vinyl propionate=45/55 mol %.

The polymer obtained was soluble in acetone, THF, ethyl acetate, methanol and R225, and was insoluble in perfluoro (2-butyltetrahydrofuran) and perfluoro-n-octane.

Example 53

2.0 g of monomer 1 obtained in Preparation Example 1, 1.82 g of vinyl propionate and 15.3 g of ethyl acetate were charged into a pressure resistant reactor made of glass and having an internal capacity of 30 mL. Then, 0.287 g of IPP was added as a polymerization initiator. The interior of the system was freeze-deaerated, followed by polymerization for 18 hours in a constant temperature shaking bath (40° C.). After the polymerization, the reaction solution was dropped into hexane to reprecipitate the polymer, followed by vacuum drying at 80° C. for 24 hours. As a result, 3.46 g of a non-crystalline polymer having a fluorinated cyclic structure in its main chain (hereinafter referred to as "polymer 6D") was obtained. The molecular weight measured by GPC employing THF as a solvent and calculated as PSt, was such that the number average molecular weight (Mn) was 6,100, and the weight average molecular weight (Mw) was 13,800, and Mw/Mn=2.24.

The polymer was a white powder at room temperature. The polymer composition calculated by $^{19}$F-NMR and $^1$H-NMR was such that repeating units made of monomer 1/repeating units made of vinyl propionate=28/72 mol %.

The polymer obtained was soluble in acetone, THF, ethyl acetate, methanol and R225, and was insoluble in perfluoro (2-butyltetrahydrofuran) and perfluoro-n-octane.

Example 54

2.0 g of monomer 16 obtained in Preparation Example 10, 0.23 g of vinyl acetate and 8.9 g of ethyl acetate were charged into a pressure resistant reactor made of glass and having an internal capacity of 30 mL. Then, 0.168 g of PFBPO was added as a polymerization initiator. The interior of the system was freeze-deaerated, followed by polymerization for 18 hours in a constant temperature shaking bath (70° C.). After the polymerization, the reaction solution was dropped into hexane to reprecipitate the polymer, followed by vacuum drying at 90° C. for 24 hours. As a result, 1.32 g of a non-crystalline polymer having a fluorinated cyclic structure in its main chain (hereinafter referred to as "polymer 7A") was obtained. The molecular weight measured by GPC employing THF as a solvent and calculated as PSt, was such that the number average molecular weight (Mn) was 4,000, and the weight average molecular weight (Mw) was 5,600, and Mw/Mn=1.41.

Tg measured by differential scanning calorimetry (DSC) was 102° C., and the polymer was a white powder at room temperature.

The polymer obtained was soluble in acetone, THF, ethyl acetate, methanol and R225, and was insoluble in perfluoro (2-butyltetrahydrofuran) and perfluoro-n-octane.

Example 55

4.0 g of monomer 16 obtained in Preparation Example 10, 1.09 g of vinyl acetate and 20.4 g of ethyl acetate were charged into a pressure resistant reactor made of glass and having an internal capacity of 50 mL. Then, 0.382 g of IPP was added as a polymerization initiator. The interior of the system was freeze-deaerated, followed by polymerization for 18 hours in a constant temperature shaking bath (40° C.). After the polymerization, the reaction solution was dropped into hexane to reprecipitate the polymer, followed by vacuum drying at 80° C. for 27 hours. As a result, 4.05 g of a non-crystalline polymer having a fluorinated cyclic structure in its main chain (hereinafter referred to as "polymer 7B") was obtained. The molecular weight measured by GPC employing a solvent as THF and calculated as PSt, was such that the number average molecular weight (Mn) was 3,700, the weight average molecular weight (Mw) was 6,000, and Mw/Mn=1.62.

Tg measured by differential scanning calorimetry (DSC) was 83° C., and the polymer was a white powder at room temperature.

The polymer obtained was soluble in acetone, THF, ethyl acetate, methanol and R225, and was insoluble in perfluoro (2-butyltetrahydrofuran) and perfluoro-n-octane.

Examples 56 to 61

1.0 g of each of polymers 5A, 6B, 6C, 6D, 7A and 7B obtained in Examples 49, 51, 52, 53, 54 and 55 was dissolved in propylene glycol monomethyl ether acetate (hereinafter referred to as "PEGMEA") to obtain a 10% solution. Then, such a solution was filtrated through a filter made of PTFE and having a pore diameter of 0.2 μm to obtain a composition for a resist protective film.

The above composition for a resist protective film was spin-coated on a CaF$_2$ substrate, followed by heat treatment at 100° C. for 90 seconds to form a resist protective film. In a transmittance measurement apparatus (spectrometer: KV-201AD type extreme ultraviolet spectroscopic measurement apparatus) flushed with nitrogen, the CaF$_2$ substrate having the obtained resist protective film formed, was placed, and the transmittances of light of 157 nm and 193 nm were measured. The results are shown in Table 6.

TABLE 6

|  | Polymer | Film thickness (nm) | Transmittance of light of 193 nm (%) | Transmittance of light of 157 nm (%) |
|---|---|---|---|---|
| Ex. 56 | 5A | 230 | 97.5 | 54.6 |
| Ex. 57 | 6B | 220 | 97.5 | 26.9 |
| Ex. 58 | 6C | 232 | 97.6 | 29.0 |
| Ex. 59 | 6D | 255 | 96.7 | 15.5 |
| Ex. 60 | 7A | 190 | 95.3 | 52.8 |
| Ex. 61 | 7B | 212 | 93.2 | 38.6 |

Examples 62 to 64

On a silicon substrate, the composition for a resist protective film prepared in each of Examples 57, 58 and 61 was spin-coated, followed by heat treatment at 100° C. for 90 seconds to form a resist protective film, whereupon the refractive index to the light beam of 193 nm was measured by a spectroscopic ellipsometer (M2000D) manufactured by J. A. Woollam Co., Inc. The results are shown in Table 7.

TABLE 7

|  | Polymer | Film thickness (nm) | Refractive index to light of 193 nm |
|---|---|---|---|
| Ex. 62 | 6B | 220 | 1.51 |
| Ex. 63 | 6C | 232 | 1.52 |
| Ex. 64 | 7B | 212 | 1.53 |

Examples 65 to 68

On a silicon substrate treated with hexamethyldisilazane, the composition for a resist protective film prepared in each of Examples 56, 57, 58 and 61 was spin-coated, followed by heat treatment at 100° C. for 90 seconds to form a resist protective film having a thickness of 0.2 μm. Then, the resist protective film on such a silicon substrate was immersed in water and alkali developer for 30 seconds, and then dried at 110° C. for 90 seconds, whereupon a change in the film thickness before and after the immersion into water and alkali developer was measured. The results are shown in Table 8.

TABLE 8

|  | Polymer | Change in film thickness after immersion into water | Change in film thickness after immersion into developer |
|---|---|---|---|
| Ex. 65 | 5A | Not changed | Changed |
| Ex. 66 | 6B | Not changed | Changed |
| Ex. 67 | 6C | Not changed | Changed |
| Ex. 68 | 7B | Not changed | Changed |

Examples 69 to 75

The polymer obtained in each of Examples 49 to 55 was dissolved in PEGMEA to obtain a 10% solution. Then, such a solution was filtrated through a filter made of PTFE and having a pore diameter of 0.2 μm, the above polymer solution was spin-coated on a silicon substrate, followed by heat treatment at 100° C. for 90 seconds to form a polymer thin film having a thickness of 0.2 μm, and then the static contact angle to water was measured. The results are shown in Table 9.

TABLE 9

|  | Polymer | Contact angle (°) |
|---|---|---|
| Ex. 69 | 5A | 77 |
| Ex. 70 | 6A | 79 |
| Ex. 71 | 6B | 81 |
| Ex. 72 | 6C | 82 |
| Ex. 73 | 6D | 81 |
| Ex. 74 | 7A | 78 |
| Ex. 75 | 7B | 81 |

Examples 76 to 82

The polymer obtained in each of Examples 49 to 55 was dissolved in PEGMEA to obtain a 10% solution. Then, such a solution was filtrated through a filter made of PTFE having a pore diameter of 0.2 μm, and the above polymer solution was spin-coated on a quartz crystal, followed by heat treatment at 100° C. for 90 seconds to form a polymer thin film having a thickness of 0.2 μm. Then, the crystal quartz was immersed in 2.38% of a tetramethyl ammonium hydroxide aqueous solution (hereinafter referred to as "TMAH solution"), whereupon the speed for dissolution of the polymer in the TMAH solution (hereinafter referred to as "developing speed") was measured by a crystal quartz microbalance (QCM). The results are shown in Table 10.

TABLE 10

|  | Polymer | Developing speed (nm/s) |
|---|---|---|
| Ex. 76 | 5A | 46 |
| Ex. 77 | 6A | 726 |
| Ex. 78 | 6B | 1,446 |
| Ex. 79 | 6C | 1,180 |
| Ex. 80 | 6D | 93 |
| Ex. 81 | 7A | 189 |
| Ex. 82 | 7B | 75 |

Comparative Example 1, Example 83

Polymer 6A obtained in Example 50 was dissolved in n-butanol to obtain a 1.0% solution (hereinafter referred to as "protective film composition 6AP").

A resist manufactured by Sumitomo Chemical Co., Ltd. (PAR715) was spin-coated on a silicon substrate treated with an organic antireflection coating (BARC), followed by heat treatment at 130° C. for 60 seconds to form a resist film (hereinafter referred to as "wafer 1X") having a thickness of 150 nm. Then, the protective film composition 6AP was further spin-coated on the resist film on the silicon substrate to form a resist protective film (hereinafter referred to as "wafer 1Y") having a thickness of 30 nm.

The above wafers 1X and 1Y were subjected to exposure tests at 90 nmL/S on drying and immersion (liquid immersion medium: ultrapure water) by a two-beam interference exposure apparatus using laser beam having a wavelength of 193 nm, whereby their pattern forms were compared by an SEM image. The results are shown in Table 11. Here, the treating conditions after the exposure are as follows.

Heating after exposure: 130° C., 60 seconds

Development: NMD-3 (23° C.), 60 seconds

TABLE 11

| | Wafer | Exposure on drying | Exposure on immersion |
|---|---|---|---|
| Comp. Ex. 1 | 1X | Good | Adhered on one portion of upper surface |
| Ex. 83 | 1Y | Good | Good |

INDUSTRIAL APPLICABILITY

The fluoropolymer of the present invention is applicable to ion exchange resins, ion exchange membranes, fuel cells, various cell materials, optical fibers, electronic members, transparent film materials, agricultural polyvinyl chloride films, adhesives, fiber materials, weather-resistant coating materials or the like, in addition to the use as a base polymer for photoresists and a polymer for a resist protective film.

The entire disclosures of Japanese Patent Application No. 2004-223363 filed on Jul. 30, 2004, Japanese Patent Application No. 2004-340595 filed on Nov. 25, 2004 and Japanese Patent Application No. 2005-151028 filed on May 24, 2005 including specifications, claims, drawings and summaries are incorporated herein by reference in their entireties.

What is claimed is:

1. A photoresist structure having a resist protective film, comprising a substrate having thereon a resist film, wherein the resist film has thereon a resist protective film, wherein the resist protective film, comprises a fluoropolymer having monomer units formed by cyclopolymerization of a fluorinated diene represented by the following formula (14) or (15):

$$CF_2=CFCF_2C(CF_3)(OR^1)\text{---}(CH_2)_nCR^2=CHR^3 \quad (14)$$

$$CF_2=CFCH_2CHQ\text{-}(CH_2)_nCR^2=CHR^3 \quad (15)$$

wherein $R^1$ is a hydrogen atom, an alkyl group having at most 20 carbon atoms, or $(CH_2)_aCOOR^4$ (wherein a is 0 or 1, and $R^4$ is a hydrogen atom or an alkyl group having at most 20 carbon atoms), each of $R^2$ and $R^3$, which are independent of each other, is a hydrogen atom or an alkyl group having at most 12 carbon atoms, Q is $(CH_2)_bC(CF_3)_c(R^5)_dOR^1$ (wherein $R^1$ is as defined above, b is an integer of from 0 to 3, c and d are integers of from 0 to 2 satisfying c+d=2, and $R^5$ is a hydrogen atom or a methyl group), provided that when $R^1$, $R^2$, $R^3$ or $R^4$ is an alkyl group, some or all of its hydrogen atoms may be substituted by fluorine atoms, or it may have an etheric oxygen atom, and n is an integer of from 0 to 2.

2. The photoresist structure of claim 1, wherein the fluoropolymer has monomer units formed by cyclopolymerization of a fluorinated diene represented by the following formula (14):

$$CF_2=CFCF_2C(CF_3)(OR^1)\text{---}(CH_2)_nCR^2=CHR^3 \quad (14).$$

3. The photoresist structure of claim 1, wherein the fluoropolymer has monomer units formed by cyclopolymerization of a fluorinated diene represented by the following formula (15):

$$CF_2=CFCH_2CHQ\text{-}(CH_2)_nCR^2=CHR^3 \quad (15).$$

4. The photoresist structure of claim 1, wherein the fluorinated diene is represented by the following formula (14-1):

$$CF_2=CFCF_2C(CF_3)(OH)\text{---}(CH_2)_nCR^2=CHR^3 \quad (14\text{-}1)$$

wherein each of $R^2$ and $R^3$, which are independent of each other, is a hydrogen atom or an alkyl group having at most 12 carbon atoms, and n is an integer of from 0 to 2.

5. The photoresist structure of claim 1, wherein the fluorinated diene is represented by the following formula (15-1):

$$CF_2=CFCH_2CH(C(CF_3)_2(OH))(CH_2)_nCR^2=CHR^3 \quad (15\text{-}1)$$

wherein each of $R^2$ and $R^3$, which are independent of each other, is a hydrogen atom or an alkyl group having at most 12 carbon atoms, and n is an integer of from 0 to 2.

6. The photoresist structure of claim 4, wherein the fluorinated diene is represented by the following formula (14-1-1) or (14-1-2):

$$CF_2=CFCF_2C(CF_3)(OH)\text{---}CH=CH^2 \quad (14\text{-}1\text{-}1)$$

$$CF_2=CFCF_2C(CF_3)(OH)\text{---}CH_2CH=CH_2 \quad (14\text{-}1\text{-}2).$$

7. The photoresist structure of claim 5, wherein the fluorinated diene is represented by the following formula (15-1-1):

$$CF_2=CFCH_2CH(C(CF_3)_2(OH))CH_2CH=CH^2 \quad (15\text{-}1\text{-}1).$$

8. The photoresist structure of claim 1, wherein the fluoropolymer is a fluorinated copolymer further comprising monomer units formed by polymerization of a vinyl ester monomer represented by the following formula (16):

$$CH_2=CHOC(O)R^8 \quad (16)$$

wherein $R^8$ is an alkyl group having at most 8 carbon atoms.

9. The photoresist structure of claim 8, wherein the vinyl ester monomer is a vinyl ester monomer represented by the following formula (16-1) or (16-2):

$$CH_2=CHOC(O)CH_3 \quad (16\text{-}1)$$

$$CH_2=CHOC(O)CH_2CH_3 \quad (16\text{-}2).$$

10. The photoresist structure of claim 1, wherein $R^1$ is a hydrogen atom or $(CH_2)_aCOOH$; and Q is $(CH_2)_bC(CF_3)_c(R^5)_dOR^1$.

* * * * *